(12) United States Patent
Murphy et al.

(10) Patent No.: US 7,754,226 B2
(45) Date of Patent: Jul. 13, 2010

(54) COMPOSITIONS AND METHODS OF USE OF ORF 554 FROM BETA HEMOLYTIC STREPTOCOCCAL STRAINS

(75) Inventors: Ellen Murphy, City Island, NY (US); Emily Mara Braunstein, New York, NY (US); Dorys Garcia-Hand, Croton-on-Hudson, NY (US); Annaliesa Sybil Anderson, Upper Saddle River, NJ (US); Ingrid Lea Dodge, Cornwall, NY (US); Eduardo Arturo Rojas, Briarcliff Manor, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/487,765

(22) Filed: Jun. 19, 2009

(65) Prior Publication Data

US 2009/0318358 A1    Dec. 24, 2009

Related U.S. Application Data

(60) Provisional application No. 61/074,239, filed on Jun. 20, 2008.

(51) Int. Cl.
    *A61K 39/09* (2006.01)
(52) U.S. Cl. .............. 424/244.1; 424/185.1; 424/190.1; 500/350; 435/975

(58) Field of Classification Search .................. None
See application file for complete search history.

(56) References Cited

FOREIGN PATENT DOCUMENTS

| WO | WO 02/34771 A2 | 5/2002 |
|---|---|---|
| WO | WO 02/083859 A2 | 10/2002 |
| WO | WO 2004/078907 A2 | 9/2004 |

OTHER PUBLICATIONS

Efstratiou A., "Outbreaks of Human Infection Caused by Pyroogenic Streptococci of Lancefield Group C and G", Journal of Medical Microbiology, vol. 29, No. 3, 1989, pp. 207-220, XP002549855.
European International Search Report—Oct. 19, 2009.

*Primary Examiner*—Jennifer E Graser
(74) *Attorney, Agent, or Firm*—Royal N. Ronning, Jr.

(57) ABSTRACT

The present invention relates to compositions and methods of use comprising peptidyl-prolyl isomerase (PPI) polypeptides of group C and G streptococci and polynucleotides encoding same. The invention also relates to immunogenic compositions comprising the PPI polypeptides and polynucleotides, as well as antibodies and antibody fragments that bind the PPI polypeptides. In addition, the invention relates to methods of inducing an immune response in a subject against beta hemolytic streptococci using the immunogenic compositions, as well as conferring passive immunity by administering a therapeutic antibody or antibody fragment.

4 Claims, No Drawings

SEQUENCE LISTING

<160> NUMBER OF SEQ ID NOS: 32

<210> SEQ ID NO 1
<211> LENGTH: 737
<212> TYPE: DNA
<213> ORGANISM: Streptococcus dysgalactiae

<400> SEQUENCE: 1

```
atgctaaacc ttgtggttag ccgtgttttt gaagctcagt atggtgataa agtatctaac      60
aaggaagtcg aaaaagctta caataaaact gctgatcagt atggtgcctc attctcagca     120
gccttggcac agtcaagctt gacaccagag acttacaaaa aacaaattcg ctcatctaaa     180
ttggttgagt atgctgtcag agaaactgct aaaaaagagt taacaactga agcatacaaa     240
aaggcttatg aaacttatac tccaacaatg gcagcacaag tgattgctct tgatagtgag     300
gaaacagcta agtctgtctt ggaagaatta aaagctgaag gcgcagattt tgctgctatt     360
gccaaagaaa aacaacagc agcagataag aaaattgctt ataaatttga ttcaggtgca     420
acaagtttac cagcagatgt tgttaaggca gcatcaggct tgaaagaagg agacatgtca     480
gaagtgattt cggtattgga tccagccact tatcaaaata aattctacat tgtcaaagtc     540
actaaaaaag ctgaaaagaa agctgactgg aaagtttata aaaaacgttt gaaagctatt     600
attctagctg aaaaaacaag agacatgaac ttccaaaaca aaatcatcgc taaagcttta     660
gacaaagcta atgttaaaat taaggacaaa gcctttgcta acatcttagt gcaatatgct     720
aaccttgata aaaaatc                                                    737
```

<210> SEQ ID NO 2
<211> LENGTH: 245
<212> TYPE: PRT
<213> ORGANISM: Streptococcus dysgalactiae

<400> SEQUENCE: 2

```
Met Leu Asn Leu Val Val Ser Arg Val Phe Glu Ala Gln Tyr Gly Asp
 1               5                  10                  15

Lys Val Ser Asn Lys Glu Val Glu Lys Ala Tyr Asn Lys Thr Ala Asp
            20                  25                  30

Gln Tyr Gly Ala Ser Phe Ser Ala Ala Leu Ala Gln Ser Ser Leu Thr
        35                  40                  45
```

-continued

Pro Glu Thr Tyr Lys Lys Gln Ile Arg Ser Ser Lys Leu Val Glu Tyr
    50                  55                  60

Ala Val Arg Glu Thr Ala Lys Lys Glu Leu Thr Thr Glu Ala Tyr Lys
65                  70                  75                  80

Lys Ala Tyr Glu Thr Tyr Thr Pro Thr Met Ala Ala Gln Val Ile Ala
                85                  90                  95

Leu Asp Ser Glu Glu Thr Ala Lys Ser Val Leu Glu Glu Leu Lys Ala
            100                 105                 110

Glu Gly Ala Asp Phe Ala Ala Ile Ala Lys Glu Lys Thr Thr Ala Ala
            115                 120                 125

Asp Lys Lys Ile Ala Tyr Lys Phe Asp Ser Gly Ala Thr Ser Leu Pro
    130                 135                 140

Ala Asp Val Val Lys Ala Ala Ser Gly Leu Lys Glu Gly Asp Met Ser
145                 150                 155                 160

Glu Val Ile Ser Val Leu Asp Pro Ala Thr Tyr Gln Asn Lys Phe Tyr
                165                 170                 175

Ile Val Lys Val Thr Lys Lys Ala Glu Lys Ala Asp Trp Lys Val
                180                 185                 190

Tyr Lys Lys Arg Leu Lys Ala Ile Ile Leu Ala Glu Lys Thr Arg Asp
    195                 200                 205

Met Asn Phe Gln Asn Lys Ile Ile Ala Lys Ala Leu Asp Lys Ala Asn
    210                 215                 220

Val Lys Ile Lys Asp Lys Ala Phe Ala Asn Ile Leu Val Gln Tyr Ala
225                 230                 235                 240

Asn Leu Asp Lys Lys
            245

<210> SEQ ID NO 3
<211> LENGTH: 759
<212> TYPE: DNA
<213> ORGANISM: Streptococcus dysgalactiae

<400> SEQUENCE: 3
tataacgaaa ccaaacacac agaagtttct caaaaggcca tgctaaacct tgtggttagc        60
cgtgtttttg aagctcagta tggtgataaa gtatctaaca aggaagtcga aaagcttac       120
aataaaactg ctgatcagta tggtgcctca ttctcagcag ccttggcaca gtcaagcttg       180
acaccagaga cttacaaaaa acaaattcgc tcatctaaat tggttgagta tgctgtcaga       240
gaaactgcta aaaagagtt aacaactgaa gcatacaaaa aggcttatga aacttatact       300
ccaacaatgg cagcacaagt gattgctctt gatagtgagg aaacagctaa gtctgtcttg       360
gaagaattaa aagctgaagg cgcagatttt gctgctattg ccaaagaaaa aacaacagca       420
gcagataaga aaattgctta taaatttgat tcaggtgcaa caagtttacc agcagatgtt       480
gttaaggcag catcaggctt gaaagaagga gacatgtcag aagtgatttc ggtattggat       540
ccagccactt atcaaaataa attctacatt gtcaaagtca ctaaaaaagc tgaaagaaa       600
gctgactgga agtttataaa aaacgtttg aaagctatta ttctagctga aaaaacaaga       660
gacatgaact ccaaaacaa aatcatcgct aaagctttag acaaagctaa tgttaaaatt       720
aaggacaaag cctttgctaa catcttagtg caatatgct                              759

<210> SEQ ID NO 4
<211> LENGTH: 253
<212> TYPE: PRT
<213> ORGANISM: Streptococcus dysgalactiae

<400> SEQUENCE: 4

```
Tyr Asn Glu Thr Lys His Thr Glu Val Ser Gln Lys Ala Met Leu Asn
1               5                   10                  15

Leu Val Val Ser Arg Val Phe Glu Ala Gln Tyr Gly Asp Lys Val Ser
            20                  25                  30

Asn Lys Glu Val Glu Lys Ala Tyr Asn Lys Thr Ala Asp Gln Tyr Gly
        35                  40                  45

Ala Ser Phe Ser Ala Ala Leu Ala Gln Ser Ser Leu Thr Pro Glu Thr
    50                  55                  60

Tyr Lys Lys Gln Ile Arg Ser Ser Lys Leu Val Glu Tyr Ala Val Arg
65                  70                  75                  80

Glu Thr Ala Lys Lys Glu Leu Thr Thr Glu Ala Tyr Lys Lys Ala Tyr
                85                  90                  95

Glu Thr Tyr Thr Pro Thr Met Ala Ala Gln Val Ile Ala Leu Asp Ser
            100                 105                 110

Glu Glu Thr Ala Lys Ser Val Leu Glu Glu Leu Lys Ala Glu Gly Ala
        115                 120                 125

Asp Phe Ala Ala Ile Ala Lys Glu Lys Thr Thr Ala Ala Asp Lys Lys
    130                 135                 140

Ile Ala Tyr Lys Phe Asp Ser Gly Ala Thr Ser Leu Pro Ala Asp Val
145                 150                 155                 160

Val Lys Ala Ala Ser Gly Leu Lys Glu Gly Asp Met Ser Glu Val Ile
                165                 170                 175

Ser Val Leu Asp Pro Ala Thr Tyr Gln Asn Lys Phe Tyr Ile Val Lys
            180                 185                 190

Val Thr Lys Lys Ala Glu Lys Ala Asp Trp Lys Val Tyr Lys Lys
        195                 200                 205

Arg Leu Lys Ala Ile Ile Leu Ala Glu Lys Thr Arg Asp Met Asn Phe
    210                 215                 220

Gln Asn Lys Ile Ile Ala Lys Ala Leu Asp Lys Ala Asn Val Lys Ile
225                 230                 235                 240

Lys Asp Lys Ala Phe Ala Asn Ile Leu Val Gln Tyr Ala
                245                 250
```

<210> SEQ ID NO 5
<211> LENGTH: 703
<212> TYPE: DNA
<213> ORGANISM: Streptococcus anginosus

<400> SEQUENCE: 5

```
agcgacttct ataacgaaac caaacacaca gaagtttctc aaaaggccat gctaaacctt    60
gtggttagcc gtgtttttga agctcagtat ggtgataaag tatctaacaa ggaagtcgaa   120
aaagcttaca ataaaactgc tgatcagtat ggtgcctcat tctcagcagc cttggcacag   180
tcaagcttga caccagagac ttacaaaaaa caaattcgct catctaaatt ggttgagtat   240
gctgtcagag aaactgctaa aaaagagtta acaactgaag catacaaaaa ggcttatgaa   300
acttatactc caacaatggc agcacaagtg attgctcttg atagtgagga aacagctaag   360
tctgtcttgg aagaattaaa agctgaaggc gcagattttg ctgctattgc caagaaaaa    420
acaacagcag cagataagaa aattgcttat aaatttgatt caggtgcaac aagtttacca   480
gcagatgttg ttaaggcagc atcaggcttg aaagaaggag acatgtcaga agtgatttcg   540
gtattggatc cagccactta tcaaaataaa ttctacattg tcaaagtcac taaaaaagct   600
gaaaagaaag ctgactggaa agtttataaa aaacgtttga agctattat tctagctgaa   660
```
aaaacaagag acatgaactt ccaaaacaaa atcatcgcta aag          703

<210> SEQ ID NO 6
<211> LENGTH: 234
<212> TYPE: PRT
<213> ORGANISM: Streptococcus anginosus

<400> SEQUENCE: 6

Ser Asp Phe Tyr Asn Glu Thr Lys His Thr Glu Val Ser Gln Lys Ala
1               5                   10                  15

Met Leu Asn Leu Val Val Ser Arg Val Phe Glu Ala Gln Tyr Gly Asp
            20                  25                  30

Lys Val Ser Asn Lys Glu Val Glu Lys Ala Tyr Asn Lys Thr Ala Asp
        35                  40                  45

Gln Tyr Gly Ala Ser Phe Ser Ala Ala Leu Ala Gln Ser Ser Leu Thr
    50                  55                  60

Pro Glu Thr Tyr Lys Lys Gln Ile Arg Ser Ser Lys Leu Val Glu Tyr
65                  70                  75                  80

Ala Val Arg Glu Thr Ala Lys Lys Glu Leu Thr Thr Glu Ala Tyr Lys
                85                  90                  95

Lys Ala Tyr Glu Thr Tyr Thr Pro Thr Met Ala Ala Gln Val Ile Ala
            100                 105                 110

Leu Asp Ser Glu Glu Thr Ala Lys Ser Val Leu Glu Leu Lys Ala
        115                 120                 125

Glu Gly Ala Asp Phe Ala Ala Ile Ala Lys Glu Lys Thr Thr Ala Ala
    130                 135                 140

Asp Lys Lys Ile Ala Tyr Lys Phe Asp Ser Gly Ala Thr Ser Leu Pro
145                 150                 155                 160

Ala Asp Val Val Lys Ala Ala Ser Gly Leu Lys Glu Gly Asp Met Ser
                165                 170                 175

Glu Val Ile Ser Val Leu Asp Pro Ala Thr Tyr Gln Asn Lys Phe Tyr
            180                 185                 190

Ile Val Lys Val Thr Lys Lys Ala Glu Lys Lys Ala Asp Trp Lys Val
        195                 200                 205

Tyr Lys Lys Arg Leu Lys Ala Ile Ile Leu Ala Glu Lys Thr Arg Asp
    210                 215                 220

Met Asn Phe Gln Asn Lys Ile Ile Ala Lys
225                 230

<210> SEQ ID NO 7
<211> LENGTH: 1056
<212> TYPE: DNA
<213> ORGANISM: Streptococcus dysgalactiae

<400> SEQUENCE: 7
atgaaaaaat caaacaaact cattgctggg attgtcacac tagcatctgt tatgactttg      60
acagcttgtc aatcaaccaa tgacaatact aaagttatct caatgaaggg tgataccatc     120
agtgtcagcg acttctataa cgaaaccaaa cacacagaag tttctcaaaa ggccatgcta     180
aaccttgtgg ttagccgtat ttttgaagct cagtatggtg ataaagtatc taacaaggaa     240
gtcgaaaaag cttacaataa aactgctgat cagtatggtg cctcattctc agcagccttg     300
gcacagtcaa gcttgacacc agagacttac aaaaaacaaa ttcgctcatc taaattggtg     360
gagtatgctg tcagagaaac tgctaaaaaa gagttaacaa ctgaagcata caaaaaggct     420
tatgaaactt atactccaac aatggcagca caagtgattg ctcttgatag tgaggaaaca     480

```
gctaagtctg tcttggaaga attaaaagct gaaggcgcag attttgctgc tattgccaaa    540
gaaaaaacaa cagcagcaga taagaaaatt gcttataaat ttgattcagg tgcaacaagt    600
ttaccagcag atgttgttaa ggcagcatca ggcttgaaag aaggagacat gtcagaagtg    660
atttcggtat tggatccagc cacttatcaa aataaattct acattgtcaa agtcactaaa    720
aaagctgaaa agaaagctga ctggaaagtt tataaaaaac gtttgaaagc tattattcta    780
gctgaaaaaa caagagacat gaacttccaa aacaaaatca tcgctaaagc tttagacaaa    840
gctaatgtta aaattaagga caaagccttt gctaacatct tagtgcaata tgctaacctt    900
gataaaaaat caaaagcaac aagttccaat tcagcaactc caaaaacatc agaagaaaaa    960
ccagcttcag aatcaacaga agctagtcag ccacaagaag aacaatctga ggcaacacca   1020
gctgaaggaa ctgctgatac tcaaacaggt gaggct                             1056
```

<210> SEQ ID NO 8
<211> LENGTH: 352
<212> TYPE: PRT
<213> ORGANISM: Streptococcus dysgalactiae

<400> SEQUENCE: 8

```
Met Lys Lys Ser Asn Lys Leu Ile Ala Gly Ile Val Thr Leu Ala Ser
1               5                   10                  15

Val Met Thr Leu Thr Ala Cys Gln Ser Thr Asn Asp Asn Thr Lys Val
            20                  25                  30

Ile Ser Met Lys Gly Asp Thr Ile Ser Val Ser Asp Phe Tyr Asn Glu
        35                  40                  45

Thr Lys His Thr Glu Val Ser Gln Lys Ala Met Leu Asn Leu Val Val
    50                  55                  60

Ser Arg Ile Phe Glu Ala Gln Tyr Gly Asp Lys Val Ser Asn Lys Glu
65                  70                  75                  80

Val Glu Lys Ala Tyr Asn Lys Thr Ala Asp Gln Tyr Gly Ala Ser Phe
                85                  90                  95

Ser Ala Ala Leu Ala Gln Ser Ser Leu Thr Pro Glu Thr Tyr Lys Lys
            100                 105                 110

Gln Ile Arg Ser Ser Lys Leu Val Glu Tyr Ala Val Arg Glu Thr Ala
        115                 120                 125

Lys Lys Glu Leu Thr Thr Glu Ala Tyr Lys Ala Tyr Glu Thr Tyr
    130                 135                 140

Thr Pro Thr Met Ala Ala Gln Val Ile Ala Leu Asp Ser Glu Glu Thr
145                 150                 155                 160

Ala Lys Ser Val Leu Glu Glu Leu Lys Ala Glu Gly Ala Asp Phe Ala
                165                 170                 175

Ala Ile Ala Lys Glu Lys Thr Thr Ala Ala Asp Lys Lys Ile Ala Tyr
            180                 185                 190

Lys Phe Asp Ser Gly Ala Thr Ser Leu Pro Ala Asp Val Val Lys Ala
        195                 200                 205

Ala Ser Gly Leu Lys Glu Gly Asp Met Ser Glu Val Ile Ser Val Leu
    210                 215                 220

Asp Pro Ala Thr Tyr Gln Asn Lys Phe Tyr Ile Val Lys Val Thr Lys
225                 230                 235                 240

Lys Ala Glu Lys Lys Ala Asp Trp Lys Val Tyr Lys Lys Arg Leu Lys
                245                 250                 255

Ala Ile Ile Leu Ala Glu Lys Thr Arg Asp Met Asn Phe Gln Asn Lys
            260                 265                 270
```

```
Ile Ile Ala Lys Ala Leu Asp Lys Ala Asn Val Lys Ile Lys Asp Lys
            275                 280                 285

Ala Phe Ala Asn Ile Leu Val Gln Tyr Ala Asn Leu Asp Lys Lys Ser
        290                 295                 300

Lys Ala Thr Ser Ser Asn Ser Ala Thr Pro Lys Thr Ser Glu Glu Lys
305                 310                 315                 320

Pro Ala Ser Glu Ser Thr Glu Ala Ser Gln Pro Gln Glu Glu Gln Ser
                325                 330                 335

Glu Ala Thr Pro Ala Glu Gly Thr Ala Asp Thr Gln Thr Gly Glu Ala
            340                 345                 350
```

<210> SEQ ID NO 9
<211> LENGTH: 1065
<212> TYPE: DNA
<213> ORGANISM: Streptococcus dysgalactiae

<400> SEQUENCE: 9

```
atgaaaaaat caaacaaact cattgctggg attgtcacac tagcatctgt tatgactttg     60
acagcttgtc aatcaactaa tgacaatacc aaagttatct caatgaaggg tgataccatc    120
agtgtcagcg acttctataa cgaaaccaaa cacacagaag tttctcaaaa ggccatgcta    180
aaccttgtgg ttagccgtgt ttttgaagct cagtatggtg ataaagtatc taacaaggaa    240
gtcgaaaaag cttacaataa aactgctgat cagtatggtg cctcattctc agcagccttg    300
gcacagtcaa gcttgacacc agagacttac aaaaaacaaa ttcgctcatc taaattggtg    360
gagtatgctg tcagagaaac tgctaaaaaa gagttaacaa ctgaagcata caaaaaggct    420
tatgaaactt atactccaac aatggcagca caagtgattg ctcttgatag tgaggaaaca    480
gctaagtctg tcttggaaga attaaaagct gaaggcgcag attttgctgc tattgccaaa    540
gaaaaaacaa cagcagcaga taagaaaatt gcttataaat ttgattcagg tgcaacaagt    600
ttaccagcag atgttgttaa ggcagcatca ggcttgaaag aaggagacat gtcagaagtg    660
atttcggtat tggatccagc cacttatcaa aataaaattct acattgtcaa agtcactaaa    720
aaagctgaaa agaaagctga ctggaaagtt tataaaaaac gtttgaaagc tattattcta    780
gctgaaaaaa caagagacat gaacttccaa aacaaaatca tcgctaaagc tttagacaaa    840
gctaatgtta aaattaagga caaagccttt gctaacatct tagtgcaata tgctaaccttt   900
gataaaaaat caaagcaac aagttccaat tcagcaactc caaaaacatc agaagaaaaa    960
ccagcttcag aatcaacaga agctagtcag ccacaagaag aacaatctga ggcaacacca   1020
gctgaaggaa ctgctgatac tcaaacaggt gaggctgctg ctcaa                    1065
```

<210> SEQ ID NO 10
<211> LENGTH: 355
<212> TYPE: PRT
<213> ORGANISM: Streptococcus dysgalactiae

<400> SEQUENCE: 10

```
Met Lys Lys Ser Asn Lys Leu Ile Ala Gly Ile Val Thr Leu Ala Ser
1               5                   10                  15

Val Met Thr Leu Thr Ala Cys Gln Ser Thr Asn Asp Asn Thr Lys Val
            20                  25                  30

Ile Ser Met Lys Gly Asp Thr Ile Ser Val Ser Asp Phe Tyr Asn Glu
        35                  40                  45

Thr Lys His Thr Glu Val Ser Gln Lys Ala Met Leu Asn Leu Val Val
    50                  55                  60
```

```
Ser Arg Val Phe Glu Ala Gln Tyr Gly Asp Lys Val Ser Asn Lys Glu
 65                  70                  75                  80

Val Glu Lys Ala Tyr Asn Lys Thr Ala Asp Gln Tyr Gly Ala Ser Phe
                 85                  90                  95

Ser Ala Ala Leu Ala Gln Ser Ser Leu Thr Pro Glu Thr Tyr Lys Lys
            100                 105                 110

Gln Ile Arg Ser Ser Lys Leu Val Glu Tyr Ala Val Arg Glu Thr Ala
        115                 120                 125

Lys Lys Glu Leu Thr Thr Glu Ala Tyr Lys Lys Ala Tyr Glu Thr Tyr
130                 135                 140

Thr Pro Thr Met Ala Ala Gln Val Ile Ala Leu Asp Ser Glu Glu Thr
145                 150                 155                 160

Ala Lys Ser Val Leu Glu Glu Leu Lys Ala Gly Ala Asp Phe Ala
                165                 170                 175

Ala Ile Ala Lys Glu Lys Thr Thr Ala Ala Asp Lys Lys Ile Ala Tyr
            180                 185                 190

Lys Phe Asp Ser Gly Ala Thr Ser Leu Pro Ala Asp Val Val Lys Ala
        195                 200                 205

Ala Ser Gly Leu Lys Glu Gly Asp Met Ser Glu Val Ile Ser Val Leu
210                 215                 220

Asp Pro Ala Thr Tyr Gln Asn Lys Phe Tyr Ile Val Lys Val Thr Lys
225                 230                 235                 240

Lys Ala Glu Lys Lys Ala Asp Trp Lys Val Tyr Lys Lys Arg Leu Lys
                245                 250                 255

Ala Ile Ile Leu Ala Glu Lys Thr Arg Asp Met Asn Phe Gln Asn Lys
            260                 265                 270

Ile Ile Ala Lys Ala Leu Asp Lys Ala Asn Val Lys Ile Lys Asp Lys
        275                 280                 285

Ala Phe Ala Asn Ile Leu Val Gln Tyr Ala Asn Leu Asp Lys Lys Ser
290                 295                 300

Lys Ala Thr Ser Ser Asn Ser Ala Thr Pro Lys Thr Ser Glu Glu Lys
305                 310                 315                 320

Pro Ala Ser Glu Ser Thr Glu Ala Ser Gln Pro Glu Glu Gln Ser
                325                 330                 335

Glu Ala Thr Pro Ala Glu Gly Thr Ala Asp Thr Gln Thr Gly Glu Ala
            340                 345                 350

Ala Ala Gln
        355

<210> SEQ ID NO 11
<211> LENGTH: 244
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (11)..(11)
<223> OTHER INFORMATION: Xaa can be Ile or Val

<400> SEQUENCE: 11

Lys Ala Met Leu Asn Leu Val Val Ser Arg Xaa Phe Glu Ala Gln Tyr
 1               5                  10                  15

Gly Asp Lys Val Ser Asn Lys Glu Val Glu Lys Ala Tyr Asn Lys Thr
                20                  25                  30

Ala Asp Gln Tyr Gly Ala Ser Phe Ser Ala Ala Leu Ala Gln Ser Ser
```

```
          35                  40                  45
Leu Thr Pro Glu Thr Tyr Lys Lys Gln Ile Arg Ser Ser Lys Leu Val
 50                  55                  60

Glu Tyr Ala Val Arg Glu Thr Ala Lys Lys Glu Leu Thr Thr Glu Ala
 65                  70                  75                  80

Tyr Lys Lys Ala Tyr Glu Thr Tyr Thr Pro Thr Met Ala Ala Gln Val
                 85                  90                  95

Ile Ala Leu Asp Ser Glu Glu Thr Ala Lys Ser Val Leu Glu Glu Leu
            100                 105                 110

Lys Ala Glu Gly Ala Asp Phe Ala Ala Ile Ala Lys Glu Lys Thr Thr
        115                 120                 125

Ala Ala Asp Lys Lys Ile Ala Tyr Lys Phe Asp Ser Gly Ala Thr Ser
130                 135                 140

Leu Pro Ala Asp Val Val Lys Ala Ala Ser Gly Leu Lys Glu Gly Asp
145                 150                 155                 160

Met Ser Glu Val Ile Ser Val Leu Asp Pro Ala Thr Tyr Gln Asn Lys
                165                 170                 175

Phe Tyr Ile Val Lys Val Thr Lys Lys Ala Glu Lys Lys Ala Asp Trp
            180                 185                 190

Lys Val Tyr Lys Lys Arg Leu Lys Ala Ile Ile Leu Ala Glu Lys Thr
        195                 200                 205

Arg Asp Met Asn Phe Gln Asn Lys Ile Ile Lys Ala Leu Asp Lys
    210                 215                 220

Ala Asn Val Lys Ile Lys Asp Lys Ala Phe Ala Asn Ile Leu Val Gln
225                 230                 235                 240

Tyr Ala Asn Leu

<210> SEQ ID NO 12
<211> LENGTH: 930
<212> TYPE: DNA
<213> ORGANISM: Streptococcus agalactiae

<400> SEQUENCE: 12
atgaaaacaa gatcaaaact tgcagcaggc tttttgacac ttatgtcagt tgccacatta      60
gctgcctgct caggtaaaac atcaaatgga acaaatgttg ttacaatgaa gggcgacact     120
atcacagtct ctgattttta tgatcaagta aaaacatcaa agctgcaca acaatcaatg      180 cttacattga tcctctcacg tgtttttgat acacagtatg gtgataaagt ttcagataaa     240
aaagtatcag aagcttataa taagacagct aaaggctatg gtaattcatt ttcagcgca     300 ctttcacaag caggtttgac tccagaaggt tacaaacaac aaattcgcac aactatgctt     360
gtggaatatg ctgtaaaaga agcagctaag aaagaattaa cagaagcaaa ctataaagaa     420
gcatatatga actataccc tgaaacttct gtacaagtaa tcaaattgga tgcagaagat     480
aaagctaaat ctgtccttaa agatgtaaag gctgatggag ctgattttgc aaagattgca     540
aaagaaaaaa caacagctac tgataaaaaa gttgagtata aatttgattc tgcagggaca     600
agcctcccta agaagttat gtcagcagcc tttaagctag ataaaatgg tgtttcagat      660 gtggtttcaa cggttgattc aacaacttat aaaacaagtt actacatcat taaagtaact     720
gataagacag agaaaaaatc tgattggaaa tcttacaaaa atcgcttaaa agaagttatt     780
cttaaggata aaacaagcga tagatccttc caaaataaag tgatttcaaa agccttagaa     840
aaagctaacg ttaagattaa agataaagca tttgcaggca tcttatcaca atatgctaca     900
acaagtggtt catcatcact taaaaaatag                                       930
```

<210> SEQ ID NO 13
<211> LENGTH: 309
<212> TYPE: PRT
<213> ORGANISM: Streptococcus agalactiae

<400> SEQUENCE: 13

Met Lys Thr Arg Ser Lys Leu Ala Ala Gly Phe Leu Thr Leu Met Ser
1               5                   10                  15

Val Ala Thr Leu Ala Ala Cys Ser Gly Lys Thr Ser Asn Gly Thr Asn
            20                  25                  30

Val Val Thr Met Lys Gly Asp Thr Ile Thr Val Ser Asp Phe Tyr Asp
        35                  40                  45

Gln Val Lys Thr Ser Lys Ala Ala Gln Ser Met Leu Thr Leu Ile
    50                  55                  60

Leu Ser Arg Val Phe Asp Thr Gln Tyr Gly Asp Lys Val Ser Asp Lys
65                  70                  75                  80

Lys Val Ser Glu Ala Tyr Asn Lys Thr Ala Lys Gly Tyr Gly Asn Ser
                85                  90                  95

Phe Ser Ser Ala Leu Ser Gln Ala Gly Leu Thr Pro Glu Gly Tyr Lys
            100                 105                 110

Gln Gln Ile Arg Thr Thr Met Leu Val Glu Tyr Ala Val Lys Glu Ala
        115                 120                 125

Ala Lys Lys Glu Leu Thr Glu Ala Asn Tyr Lys Glu Ala Tyr Lys Asn
    130                 135                 140

Tyr Thr Pro Glu Thr Ser Val Gln Val Ile Lys Leu Asp Ala Glu Asp
145                 150                 155                 160

Lys Ala Lys Ser Val Leu Lys Asp Val Lys Ala Asp Gly Ala Asp Phe
                165                 170                 175

Ala Lys Ile Ala Lys Glu Lys Thr Thr Ala Thr Asp Lys Lys Val Glu
            180                 185                 190

Tyr Lys Phe Asp Ser Ala Gly Thr Ser Leu Pro Lys Glu Val Met Ser
        195                 200                 205

Ala Ala Phe Lys Leu Asp Lys Asn Gly Val Ser Asp Val Val Ser Thr
    210                 215                 220

Val Asp Ser Thr Thr Tyr Lys Thr Ser Tyr Tyr Ile Ile Lys Val Thr
225                 230                 235                 240

Asp Lys Thr Glu Lys Lys Ser Asp Trp Lys Ser Tyr Lys Asn Arg Leu
                245                 250                 255

Lys Glu Val Ile Leu Lys Asp Lys Thr Ser Asp Arg Ser Phe Gln Asn
            260                 265                 270

Lys Val Ile Ser Lys Ala Leu Glu Lys Ala Asn Val Lys Ile Lys Asp
        275                 280                 285

Lys Ala Phe Ala Gly Ile Leu Ser Gln Tyr Ala Thr Thr Ser Gly Ser
    290                 295                 300

Ser Ser Leu Lys Lys
305

<210> SEQ ID NO 14
<211> LENGTH: 1056
<212> TYPE: DNA
<213> ORGANISM: Streptococcus pyogenes

<400> SEQUENCE: 14
atgaaaaact caaataaact cattgctagt gttgtgacat tggcctcagt gatggcttta    60

```
gcagcttgtc aatcaactaa tgacaatact aaggttattt cgatgaaagg tgatacaatt      120
agcgttagtg atttttacaa tgaaacaaaa aacacagaag tatcgcaaaa agcgatgcta      180
aatctggtaa ttagtcgtgt ttttgaagct caatatggtg ataaggtttc aaaaaaagaa      240
gttgaaaagg cgtatcataa aacagctgaa cagtatggcg cttcattctc tgctgctttg      300
gcacaatcaa gcttgacacc tgagactttt aagcgtcaga tccgctcttc aaaattagta      360
gaatatgcgg ttaagaaagc agctaaaaaa gaattgacaa cacaagaata taagaaagca      420
tatgaatctt atactccaac aatggcagtc gaaatgatta ctttagataa tgaagagaca      480
gctaaatcag tcttagagga actaaaagcc gaaggcgcag actttacagc tattgctaaa      540
gaaaaaacaa caacacctga aaaaaagtg acctataaat ttgattcagg tgcgacaaat      600
gtaccgactg atgtcgtaaa agcggcttca agtttgaatg agggtggcat atcagacgtt      660
atctcggttt tagatccaac ttcttatcaa aagaagttttt acattgttaa ggtgactaaa      720
aaagcagaaa aaaatcaga ttggcaagaa tataagaaac gtttgaaagc tatcattata      780
gctgaaaaat caaagatat gaatttccaa aacaaggtta ttgcaaatgc attggataaa      840
gctaatgtaa aaattaaaga caaagctttt gctaatattt tggcgcaata tgcaaatctt      900
ggtcaaaaaa ctaaagctgc aagtgaaagt tcaacaacca gcgaatcatc aaaagctgca      960
gaagagaacc catcagaatc agagcaaaca cagacatcat cagctgaaga accaactgag     1020
actgaggctc agacgcaaga gccagctgca caataa                               1056
```

<210> SEQ ID NO 15
<211> LENGTH: 351
<212> TYPE: PRT
<213> ORGANISM: Streptococcus pyogenes

<400> SEQUENCE: 15

```
Met Lys Asn Ser Asn Lys Leu Ile Ala Ser Val Thr Leu Ala Ser
 1               5                  10                  15

Val Met Ala Leu Ala Ala Cys Gln Ser Thr Asn Asp Asn Thr Lys Val
                20                  25                  30

Ile Ser Met Lys Gly Asp Thr Ile Ser Val Ser Asp Phe Tyr Asn Glu
            35                  40                  45

Thr Lys Asn Thr Glu Val Ser Gln Lys Ala Met Leu Asn Leu Val Ile
        50                  55                  60

Ser Arg Val Phe Glu Ala Gln Tyr Gly Asp Lys Val Ser Lys Glu
65                  70                  75                  80

Val Glu Lys Ala Tyr His Lys Thr Ala Glu Gln Tyr Gly Ala Ser Phe
                85                  90                  95

Ser Ala Ala Leu Ala Gln Ser Ser Leu Thr Pro Glu Thr Phe Lys Arg
            100                 105                 110

Gln Ile Arg Ser Ser Lys Leu Val Glu Tyr Ala Val Lys Glu Ala Ala
        115                 120                 125

Lys Lys Glu Leu Thr Thr Gln Glu Tyr Lys Lys Ala Tyr Glu Ser Tyr
    130                 135                 140

Thr Pro Thr Met Ala Val Glu Met Ile Thr Leu Asp Asn Glu Glu Thr
145                 150                 155                 160

Ala Lys Ser Val Leu Glu Glu Leu Lys Ala Glu Gly Ala Asp Phe Thr
                165                 170                 175

Ala Ile Ala Lys Glu Lys Thr Thr Thr Pro Glu Lys Lys Val Thr Tyr
            180                 185                 190

Lys Phe Asp Ser Gly Ala Thr Asn Val Pro Thr Asp Val Val Lys Ala
```

```
                        195                 200                 205
Ala Ser Ser Leu Asn Glu Gly Gly Ile Ser Asp Val Ile Ser Val Leu
    210                 215                 220

Asp Pro Thr Ser Tyr Gln Lys Lys Phe Tyr Ile Val Lys Val Thr Lys
225                 230                 235                 240

Lys Ala Glu Lys Lys Ser Asp Trp Gln Glu Tyr Lys Lys Arg Leu Lys
                245                 250                 255

Ala Ile Ile Ile Ala Glu Lys Ser Lys Asp Met Asn Phe Gln Asn Lys
            260                 265                 270

Val Ile Ala Asn Ala Leu Asp Lys Ala Asn Val Lys Ile Lys Asp Lys
        275                 280                 285

Ala Phe Ala Asn Ile Leu Ala Gln Tyr Ala Asn Leu Gly Gln Lys Thr
    290                 295                 300

Lys Ala Ala Ser Glu Ser Ser Thr Thr Ser Glu Ser Ser Lys Ala Ala
305                 310                 315                 320

Glu Glu Asn Pro Ser Glu Ser Glu Gln Thr Gln Thr Ser Ser Ala Glu
                325                 330                 335

Glu Pro Thr Glu Thr Glu Ala Gln Thr Gln Glu Pro Ala Ala Gln
            340                 345                 350

<210> SEQ ID NO 16
<211> LENGTH: 999
<212> TYPE: DNA
<213> ORGANISM: Streptococcus zooepidemicus

<400> SEQUENCE: 16
atgaaaaaat caactaaatt acttgctggt atagtaaccc tagcatcagc aatgaccota      60 gcagcctgtc agtctacaaa tgacaacaca gtgtcatta cgatgaaggg cgacactatc     120
agtgttagtg attttttacaa cgaaacaaaa aatacagagg tttctcaaag agcaatgcta     180
aaccttgtgg ttagtcgtgt ttttgaggac caatacggta aaaaggtttc taagaaaaaa     240
acagaagaag cctacaataa atcagctgag caatacggtg cgtcattctc tgcagccctt     300
gcgcagtctg gcttgacaac agatacctac aagcgtcaaa ttcgctcagc catgctggtt     360
gaatatgctg ttaaagaagc agctaaaaaa gagctaacag atgctgatta caaaaaagcc     420
tatgagtcat acacaccaga atgactact caggtcatta ctctagacaa tgaagaaaca     480
gctaaggcta ttttaggtga ggttaaggct gagggtgctg actttgctgc tattgctaag     540
gaaaagacaa cagcagcaga caagaaggta gactataagt ttgattcagg agatactaag     600
ttaccagcag atgtgatcaa agccgcttca ggattaaaag agggtgatat tcagaggtg      660 gtttcagttc tagatccagc gacctaccaa acaaattct atattgttaa ggtaaccaaa     720
aaagctgaaa aggcttctga ttggaagaaa tataagaaac gtttgaaaga aattgtcttg     780
gctgaaaaga cacaaaacat tgatttccaa aacaaggtca ttgcaaaggc tttagataaa     840
gcaaatgtta agatcaaaga ccaagccttt gctaatatct ggcacagta tgccaatact     900 gataaaaaag caagcaaggc gaacacaagc aagtcagatc aaaaaacatc ttcagactca     960
agcaaggaca gtcaatcttc caaatctaaa tcagaaaaa                             999

<210> SEQ ID NO 17
<211> LENGTH: 333
<212> TYPE: PRT
<213> ORGANISM: Streptococcus zooepidemicus

<400> SEQUENCE: 17
```

```
Met Lys Lys Ser Thr Lys Leu Leu Ala Gly Ile Val Thr Leu Ala Ser
1               5                   10                  15

Ala Met Thr Leu Ala Ala Cys Gln Ser Thr Asn Asp Asn Thr Ser Val
            20                  25                  30

Ile Thr Met Lys Gly Asp Thr Ile Ser Val Ser Asp Phe Tyr Asn Glu
            35                  40                  45

Thr Lys Asn Thr Glu Val Ser Gln Arg Ala Met Leu Asn Leu Val Val
50                  55                  60

Ser Arg Val Phe Glu Asp Gln Tyr Gly Lys Lys Val Ser Lys Lys Lys
65                  70                  75                  80

Thr Glu Glu Ala Tyr Asn Lys Ser Ala Glu Gln Tyr Gly Ala Ser Phe
                85                  90                  95

Ser Ala Ala Leu Ala Gln Ser Gly Leu Thr Thr Asp Thr Tyr Lys Arg
            100                 105                 110

Gln Ile Arg Ser Ala Met Leu Val Glu Tyr Ala Val Lys Glu Ala Ala
            115                 120                 125

Lys Lys Glu Leu Thr Asp Ala Asp Tyr Lys Lys Ala Tyr Glu Ser Tyr
130                 135                 140

Thr Pro Glu Met Thr Thr Gln Val Ile Thr Leu Asp Asn Glu Glu Thr
145                 150                 155                 160

Ala Lys Ala Ile Leu Gly Glu Val Lys Ala Glu Gly Ala Asp Phe Ala
                165                 170                 175

Ala Ile Ala Lys Glu Lys Thr Thr Ala Ala Asp Lys Lys Val Asp Tyr
            180                 185                 190

Lys Phe Asp Ser Gly Asp Thr Lys Leu Pro Ala Asp Val Ile Lys Ala
            195                 200                 205

Ala Ser Gly Leu Lys Glu Gly Asp Ile Ser Glu Val Val Ser Val Leu
210                 215                 220

Asp Pro Ala Thr Tyr Gln Asn Lys Phe Tyr Ile Val Lys Val Thr Lys
225                 230                 235                 240

Lys Ala Glu Lys Ala Ser Asp Trp Lys Lys Tyr Lys Lys Arg Leu Lys
                245                 250                 255

Glu Ile Val Leu Ala Glu Lys Thr Gln Asn Ile Asp Phe Gln Asn Lys
            260                 265                 270

Val Ile Ala Lys Ala Leu Asp Lys Ala Asn Val Lys Ile Lys Asp Gln
            275                 280                 285

Ala Phe Ala Asn Ile Leu Ala Gln Tyr Ala Asn Thr Asp Lys Lys Ala
            290                 295                 300

Ser Lys Ala Asn Thr Ser Lys Ser Asp Gln Lys Thr Ser Ser Asp Ser
305                 310                 315                 320

Ser Lys Asp Ser Gln Ser Ser Ser Lys Ser Glu Lys
                325                 330
```

<210> SEQ ID NO 18
<211> LENGTH: 19
<212> TYPE: DNA
<213> ORGANISM: artificial
<220> FEATURE:
<223> OTHER INFORMATION: degenerate primer corresponding to position 61 of ORF554

<400> SEQUENCE: 18
gcytgtcart cwacwaatg                                                19

<210> SEQ ID NO 19
<211> LENGTH: 17

```
<212> TYPE: DNA
<213> ORGANISM: artificial
<220> FEATURE:
<223> OTHER INFORMATION: degenerate primer corresponding to position 101
      of ORF554

<400> SEQUENCE: 19
atgaarggyg ayacwat                                                  17

<210> SEQ ID NO 20
<211> LENGTH: 18
<212> TYPE: DNA
<213> ORGANISM: artificial
<220> FEATURE:
<223> OTHER INFORMATION: degenerate primer corresponding to position 533
      of ORF554

<400> SEQUENCE: 20
gcwaargaaa aracaaca                                                 18

<210> SEQ ID NO 21
<211> LENGTH: 18
<212> TYPE: DNA
<213> ORGANISM: artificial
<220> FEATURE:
<223> OTHER INFORMATION: degenerate primer (reverse) corresponding to
      position 510 of ORF554

<400> SEQUENCE: 21
tgttgtyttt tcyttwgc                                                 18

<210> SEQ ID NO 22
<211> LENGTH: 21
<212> TYPE: DNA
<213> ORGANISM: artificial
<220> FEATURE:
<223> OTHER INFORMATION: degenerate primer (reverse) corresponding to
      position 952 of ORF554

<400> SEQUENCE: 22
ctrtsyttgc tctgaktctg a                                             21

<210> SEQ ID NO 23
<211> LENGTH: 25
<212> TYPE: DNA
<213> ORGANISM: artificial
<220> FEATURE:
<223> OTHER INFORMATION: PCR forward primer

<400> SEQUENCE: 23
atcagtgtca gcgacttcta taacg                                         25

<210> SEQ ID NO 24
<211> LENGTH: 18
<212> TYPE: DNA
<213> ORGANISM: artificial
<220> FEATURE:
<223> OTHER INFORMATION: reverse PCR primer

<400> SEQUENCE: 24
gttgctgatt ggaacttg                                                 18

<210> SEQ ID NO 25
<211> LENGTH: 1068
<212> TYPE: DNA
<213> ORGANISM: Streptococcus dysgalactiae
```

-continued

```
<400> SEQUENCE: 25
atgaaaaaat caaacaaact cattgctggg attgtcacac tagcatctgt tatgactttg    60
acagcttgtc aatcaactaa tgacaatacc aaagttatct caatgaaggg tgataccatc   120
agtgtcagcg acttctataa cgaaaccaaa cacacagaag tttctcaaaa ggccatgcta   180
aaccttgtgg ttagccgtgt ttttgaagct cagtatggtg ataaagtatc taacaaggaa   240
gtcgaaaaag cttacaataa aactgctgat cagtatggtg cctcattctc agcagccttg   300
gcacagtcaa gcttgacacc agagacttac aaaaaacaaa ttcgctcatc taaattggtt   360
gagtatgctg tcagagaaac tgctaaaaaa gagttaacaa ctgaagcata caaaaaggct   420
tatgaaactt atactccaac aatggcagca caagtgattg ctcttgatag tgaggaaaca   480
gctaagtctg tcttggaaga attaaaagct gaaggcgcag attttgctgc tattgccaaa   540
gaaaaaacaa cagcagcaga taagaaaatt gcttataaat ttgattcagg tgcaacaagt   600
ttaccagcag atgttgttaa ggcagcatca ggcttgaaag aaggagacat gtcagaagtg   660
atttcggtat tggatccagc cacttatcaa aataaattct acattgtcaa agtcactaaa   720
aaagctgaaa agaaagctga ctggaaagtt tataaaaaac gtttgaaagc tattattcta   780
gctgaaaaaa caagagacat gaacttccaa aacaaaatca tcgctaaagc tttagacaaa   840
gctaatgtta aaattaagga caaagccttt gctaacatct tagtgcaata tgctaacctt   900
gataaaaaat caaaagcaac aagttccaat tcagcaactc caaaaacatc agaagaaaaa   960
ccagcttcag aatcaacaga agctagtcag ccacaagaag aacaatctga ggcaacacca  1020
gctgaaggaa ctgctgatac tcaaacaggt gaggctgctg ctcaataa              1068

<210> SEQ ID NO 26
<211> LENGTH: 355
<212> TYPE: PRT
<213> ORGANISM: Streptococcus dysgalactiae

<400> SEQUENCE: 26

Met Lys Lys Ser Asn Lys Leu Ile Ala Gly Ile Val Thr Leu Ala Ser
1               5                   10                  15

Val Met Thr Leu Thr Ala Cys Gln Ser Thr Asn Asp Asn Thr Lys Val
                20                  25                  30

Ile Ser Met Lys Gly Asp Thr Ile Ser Val Ser Asp Phe Tyr Asn Glu
            35                  40                  45

Thr Lys His Thr Glu Val Ser Gln Lys Ala Met Leu Asn Leu Val Val
        50                  55                  60

Ser Arg Val Phe Glu Ala Gln Tyr Gly Asp Lys Val Ser Asn Lys Glu
65                  70                  75                  80

Val Glu Lys Ala Tyr Asn Lys Thr Ala Asp Gln Tyr Gly Ala Ser Phe
                85                  90                  95

Ser Ala Ala Leu Ala Gln Ser Ser Leu Thr Pro Glu Thr Tyr Lys Lys
                100                 105                 110

Gln Ile Arg Ser Ser Lys Leu Val Glu Tyr Ala Val Arg Glu Thr Ala
            115                 120                 125

Lys Lys Glu Leu Thr Thr Glu Ala Tyr Lys Lys Ala Tyr Glu Thr Tyr
        130                 135                 140

Thr Pro Thr Met Ala Ala Gln Val Ile Ala Leu Asp Ser Glu Glu Thr
145                 150                 155                 160

Ala Lys Ser Val Leu Glu Glu Leu Lys Ala Glu Gly Ala Asp Phe Ala
                165                 170                 175
```

```
Ala Ile Ala Lys Glu Lys Thr Thr Ala Ala Asp Lys Lys Ile Ala Tyr
            180                 185                 190
Lys Phe Asp Ser Gly Ala Thr Ser Leu Pro Ala Asp Val Val Lys Ala
        195                 200                 205
Ala Ser Gly Leu Lys Glu Gly Asp Met Ser Glu Val Ile Ser Val Leu
    210                 215                 220
Asp Pro Ala Thr Tyr Gln Asn Lys Phe Tyr Ile Val Lys Val Thr Lys
225                 230                 235                 240
Lys Ala Glu Lys Lys Ala Asp Trp Lys Val Tyr Lys Lys Arg Leu Lys
                245                 250                 255
Ala Ile Ile Leu Ala Glu Lys Thr Arg Asp Met Asn Phe Gln Asn Lys
            260                 265                 270
Ile Ile Ala Lys Ala Leu Asp Lys Ala Asn Val Lys Ile Lys Asp Lys
        275                 280                 285
Ala Phe Ala Asn Ile Leu Val Gln Tyr Ala Asn Leu Asp Lys Lys Ser
    290                 295                 300
Lys Ala Thr Ser Ser Asn Ser Ala Thr Pro Lys Thr Ser Glu Glu Lys
305                 310                 315                 320
Pro Ala Ser Glu Ser Thr Glu Ala Ser Gln Pro Gln Glu Glu Gln Ser
                325                 330                 335
Glu Ala Thr Pro Ala Glu Gly Thr Ala Asp Thr Gln Thr Gly Glu Ala
            340                 345                 350
Ala Ala Gln
    355

<210> SEQ ID NO 27
<211> LENGTH: 1068
<212> TYPE: DNA
<213> ORGANISM: Streptococcus dysgalactiae

<400> SEQUENCE: 27
atgaaaaaat caaacaaact cattgctggg attgtcacac tagcatctgt tatgactttg      60
acagcttgtc aatcaactaa tgacaatacc aaagttatct caatgaaggg tgataccatc     120
agtgtcagcg acttctataa cgaaaccaaa cacacagaag tttctcaaaa ggctatgcta     180
aaccttgtgg ttagccgtgt ttttgaagct cagtatggtg ataaagtatc taacaaggaa     240
gtcgaaaaag cttacaataa aactgctgat cagtatggtg cctcattctc agcagccttg     300
gcacagtcaa gcttgacacc agagacttac aaaaaacaaa ttcgctcatc taaattggtg     360
gagtatgctg tcagagaaac tgctaaaaaa gagttaacaa ctgaagcata caaaaaggct     420
tatgaaactt atactccaac aatggcagca caagtgattg ctcttgatag tgaggaaaca     480
gctaagtctg tcttggaaga attaaaagct gaaggcgcag attttgctgc tattgccaaa     540
gaaaaaacaa cagcagcaga taagaaaatt gcttataaat ttgattcagg tgcaacaagt     600
ttaccagcag atgttgttaa ggcagcatca ggcttgaaag aaggagacat gtcagaagtg     660
atttcggtat tggatccagc cacttatcaa ataaaattct acattgtcaa agtcactaaa     720
aaagctgaaa agaaagctga ctggaaagtt tataaaaaac gtttgaaagc tattattcta     780
gctgaaaaaa caagagacat gaacttccaa aacaaaatca tcgctaaagc tttagacaaa     840
gctaatgtta aaattaagga caaagccttt gctaacatct tagtgcaata tgctaacctt     900
gataaaaaat caaagcaac aagttccaat tcagcaactc caaaaacatc agaagaaaaa     960
ccagcttcag aatcaacaga agctagtcag ccacaagaag aacaatctga ggcaacacca    1020
gctgaaggaa ctgctgatac tcaaacaggt gaggctgctg ctcaataa                1068
```

<210> SEQ ID NO 28
<211> LENGTH: 355
<212> TYPE: PRT
<213> ORGANISM: Streptococcus dysgalactiae

<400> SEQUENCE: 28

Met Lys Lys Ser Asn Lys Leu Ile Ala Gly Ile Val Thr Leu Ala Ser
1               5                   10                  15

Val Met Thr Leu Thr Ala Cys Gln Ser Thr Asn Asp Asn Thr Lys Val
            20                  25                  30

Ile Ser Met Lys Gly Asp Thr Ile Ser Val Ser Asp Phe Tyr Asn Glu
        35                  40                  45

Thr Lys His Thr Glu Val Ser Gln Lys Ala Met Leu Asn Leu Val Val
    50                  55                  60

Ser Arg Val Phe Glu Ala Gln Tyr Gly Asp Lys Val Ser Asn Lys Glu
65                  70                  75                  80

Val Glu Lys Ala Tyr Asn Lys Thr Ala Asp Gln Tyr Gly Ala Ser Phe
                85                  90                  95

Ser Ala Ala Leu Ala Gln Ser Ser Leu Thr Pro Glu Thr Tyr Lys Lys
            100                 105                 110

Gln Ile Arg Ser Ser Lys Leu Val Glu Tyr Ala Val Arg Glu Thr Ala
        115                 120                 125

Lys Lys Glu Leu Thr Thr Glu Ala Tyr Lys Lys Ala Tyr Glu Thr Tyr
    130                 135                 140

Thr Pro Thr Met Ala Ala Gln Val Ile Ala Leu Asp Ser Glu Glu Thr
145                 150                 155                 160

Ala Lys Ser Val Leu Glu Glu Leu Lys Ala Glu Gly Ala Asp Phe Ala
                165                 170                 175

Ala Ile Ala Lys Glu Lys Thr Thr Ala Ala Asp Lys Lys Ile Ala Tyr
            180                 185                 190

Lys Phe Asp Ser Gly Ala Thr Ser Leu Pro Ala Asp Val Val Lys Ala
        195                 200                 205

Ala Ser Gly Leu Lys Glu Gly Asp Met Ser Glu Val Ile Ser Val Leu
    210                 215                 220

Asp Pro Ala Thr Tyr Gln Asn Lys Phe Tyr Ile Val Lys Val Thr Lys
225                 230                 235                 240

Lys Ala Glu Lys Lys Ala Asp Trp Lys Val Tyr Lys Lys Arg Leu Lys
                245                 250                 255

Ala Ile Ile Leu Ala Glu Lys Thr Arg Asp Met Asn Phe Gln Asn Lys
            260                 265                 270

Ile Ile Ala Lys Ala Leu Asp Lys Ala Asn Val Lys Ile Lys Asp Lys
        275                 280                 285

Ala Phe Ala Asn Ile Leu Val Gln Tyr Ala Asn Leu Asp Lys Lys Ser
    290                 295                 300

Lys Ala Thr Ser Ser Asn Ser Ala Thr Pro Lys Thr Ser Glu Glu Lys
305                 310                 315                 320

Pro Ala Ser Glu Ser Thr Glu Ala Ser Gln Pro Gln Glu Gln Ser
                325                 330                 335

Glu Ala Thr Pro Ala Glu Gly Thr Ala Asp Thr Gln Thr Gly Glu Ala
            340                 345                 350

Ala Ala Gln
        355

<210> SEQ ID NO 29
<211> LENGTH: 936
<212> TYPE: DNA
<213> ORGANISM: Streptococcus anginosus

<400> SEQUENCE: 29

```
atgaagaaaa aaattctagc aggagccatt acgcttttgt cagttgtaac attagcggca      60
tgctcgcaag ctggtggtaa agatattatc acgatgaaag aaatacaat tactgtcaat      120
gatttctata caaagtaaa aaataatgca gctgctcaac aagtacttct caatatgacc      180
attcaagaag ttttgaaaa gagctatggt aaacatgtta cagaaaaaga agtcaatgaa      240
acgttcaata agagtaagag cacttacgga actgctttcc aacaagtatt ggcaagagca      300
ggattgacgg aagatactta tcgtgaacaa atcagaacca ataaattggt cgaatatgct      360
gtcaaaaaag cagctgaaaa agaattgaca gatgcaaact ataaaaagc atacgaatct      420
tatacaccag aagtgactgc tcaaatcatc aaagttgaca gtcaagacaa ggcaaaggaa      480
gtactggaaa agctaaagc tgaaggtgct gatttcggac aaattgccaa ggaaaattct      540
acggatacga agaccaaaga taagggtggg aagtgaagt ttgactcagc ttcgacagat      600
gttccagatg ctgttaaaaa ggcggctttt gctcttgaag caaacggtat ttcggatgtt      660
atcaccgtta atcatcaac ttattcttca agttattata ttgtgaaact aaatagtaaa      720
tctgaaaaat cagcaaactg aaagactac aagaaacaac tgaaaaatgt tatcttgaca      780
caaaaacaaa atgatcgcac ctttattcaa aaaattgttg ccaaagaatt acaagcagcc      840
aatattaagg tgaaagatca gctttccaa agtctattct cacaatatgt caagtcagat      900
agcaaatcaa catctagctc gtcatcttca tcaaaa                             936
```

<210> SEQ ID NO 30
<211> LENGTH: 312
<212> TYPE: PRT
<213> ORGANISM: Streptococcus anginosus

<400> SEQUENCE: 30

```
Met Lys Lys Lys Ile Leu Ala Gly Ala Ile Thr Leu Leu Ser Val Val
1               5                   10                  15

Thr Leu Ala Ala Cys Ser Gln Ala Gly Gly Lys Asp Ile Ile Thr Met
            20                  25                  30

Lys Gly Asn Thr Ile Thr Val Asn Asp Phe Tyr Asn Lys Val Lys Asn
        35                  40                  45

Asn Ala Ala Ala Gln Gln Val Leu Leu Asn Met Thr Ile Gln Glu Val
    50                  55                  60

Phe Glu Lys Ser Tyr Gly Lys His Val Thr Glu Lys Val Asn Glu
65                  70                  75                  80

Thr Phe Asn Lys Ser Lys Ser Thr Tyr Gly Thr Ala Phe Gln Gln Val
                85                  90                  95

Leu Ala Arg Ala Gly Leu Thr Glu Asp Thr Tyr Arg Glu Gln Ile Arg
            100                 105                 110

Thr Asn Lys Leu Val Glu Tyr Ala Val Lys Ala Ala Glu Lys Glu
        115                 120                 125

Leu Thr Asp Ala Asn Tyr Lys Lys Ala Tyr Glu Ser Tyr Thr Pro Glu
    130                 135                 140

Val Thr Ala Gln Ile Ile Lys Val Asp Ser Gln Asp Lys Ala Lys Glu
145                 150                 155                 160

Val Leu Glu Lys Ala Lys Ala Glu Gly Ala Asp Phe Gly Gln Ile Ala
                165                 170                 175
```

Lys Glu Asn Ser Thr Asp Thr Lys Thr Lys Asp Lys Gly Gly Glu Val
                180                 185                 190

Lys Phe Asp Ser Ala Ser Thr Asp Val Pro Asp Ala Val Lys Lys Ala
                195                 200                 205

Ala Phe Ala Leu Glu Ala Asn Gly Ile Ser Asp Val Ile Thr Val Lys
                210                 215                 220

Ser Ser Thr Tyr Ser Ser Ser Tyr Tyr Ile Val Lys Leu Asn Ser Lys
225                 230                 235                 240

Ser Glu Lys Ser Ala Asn Trp Lys Asp Tyr Lys Lys Gln Leu Lys Asn
                245                 250                 255

Val Ile Leu Thr Gln Lys Gln Asn Asp Arg Thr Phe Ile Gln Lys Ile
                260                 265                 270

Val Ala Lys Glu Leu Gln Ala Ala Asn Ile Lys Val Lys Asp Gln Ala
                275                 280                 285

Phe Gln Ser Leu Phe Ser Gln Tyr Val Lys Ser Asp Ser Lys Ser Thr
                290                 295                 300

Ser Ser Ser Ser Ser Ser Ser Lys
305                 310

<210> SEQ ID NO 31
<211> LENGTH: 300
<212> TYPE: DNA
<213> ORGANISM: Streptococcus constellatus

<400> SEQUENCE: 31
atgaagaaaa aaattctagc aggagctatt acgcttttgt cagttgtaac attagcagca      60
tgctcacaag ctggtggtaa agacattatc acgatgaagg gaaatacaat tactgtcagt     120 gattttata ataaagtaaa aaataatgca gctgctcaac aagtacttct caatatgacc      180
attcaagaag tttttgaaaa gagttatggt aagcatgtta cagaaaaaga agtcactgaa     240
acgttcaata gagtaagag cacttacgga actgcttttc aacaagtatt ggcaagagca     300

<210> SEQ ID NO 32
<211> LENGTH: 312
<212> TYPE: PRT
<213> ORGANISM: Streptococcus constellatus

<400> SEQUENCE: 32

Met Lys Lys Lys Ile Leu Ala Gly Ala Ile Thr Leu Leu Ser Val Val
1               5                   10                  15

Thr Leu Ala Ala Cys Ser Gln Ala Gly Gly Lys Asp Ile Ile Thr Met
                20                  25                  30

Lys Gly Asn Thr Ile Thr Val Ser Asp Phe Tyr Asn Lys Val Lys Asn
                35                  40                  45

Asn Ala Ala Ala Gln Gln Val Leu Leu Asn Met Thr Ile Gln Glu Val
                50                  55                  60

Phe Glu Lys Ser Tyr Gly Lys His Val Thr Glu Lys Glu Val Thr Glu
65                  70                  75                  80

Thr Phe Asn Lys Ser Lys Ser Thr Tyr Gly Thr Ala Phe Gln Gln Val
                85                  90                  95

Leu Ala Arg Ala Gly Leu Thr Glu Asp Thr Tyr Arg Glu Gln Ile Arg
                100                 105                 110

Thr Asn Lys Leu Val Glu Tyr Ala Val Lys Ala Ala Glu Lys Glu
                115                 120                 125

Leu Thr Asp Ala Asn Tyr Lys Lys Ala Tyr Glu Ser Tyr Thr Pro Glu

-continued

```
                130             135             140
Val Thr Ala Gln Ile Ile Lys Val Asp Asn Gln Asp Lys Ala Lys Glu
145                 150                 155                 160

Val Leu Ala Lys Ala Lys Ala Glu Gly Ala Asp Phe Gly Gln Ile Ala
                165                 170                 175

Lys Glu Asn Ser Thr Asp Lys Lys Thr Lys Asp Lys Gly Gly Glu Val
                180                 185                 190

Lys Phe Asp Ser Ala Ser Thr Asp Val Pro Asp Ala Val Lys Lys Ala
                195                 200                 205

Ala Phe Ala Leu Glu Ala Asn Gly Ile Ser Asp Val Ile Thr Val Lys
                210                 215                 220

Ser Ser Thr Tyr Ser Ser Ser Tyr Tyr Ile Val Lys Leu Asn Ser Lys
225                 230                 235                 240

Ser Glu Lys Ser Ala Asn Trp Lys Asp Tyr Lys Lys Gln Leu Lys Asn
                245                 250                 255

Val Ile Leu Thr Gln Lys Gln Asn Asn Arg Thr Phe Ile Gln Arg Ile
                260                 265                 270

Val Ala Lys Glu Leu Gln Ala Ala Asn Ile Lys Val Lys Asp Gln Ala
                275                 280                 285

Phe Gln Asn Leu Phe Ser Gln Tyr Val Lys Ser Asp Ser Lys Ser Thr
                290                 295                 300

Ser Ser Ser Ser Ser Ser Ser Lys
305                 310
```

COMPOSITIONS AND METHODS OF USE OF ORF 554 FROM BETA HEMOLYTIC STREPTOCOCCAL STRAINS

CROSS-REFERENCE TO RELATED APPLICATIONS

This application claims priority from U.S. Provisional Application No. 61/074,239, filed on Jun. 20, 2008. The provisional application is incorporated herein by reference in its entirety.

BACKGROUND

The present invention generally relates to the fields of bacteriology, infectious disease and immunology. More particularly, the invention relates to polynucleotides, polypeptides and immunogenic compositions comprising a beta hemolytic streptococci polypeptide.

The beta hemolytic *Streptococcus* (BHS) species are important pathogens responsible for numerous human diseases ranging from superficial infections to more severe illnesses. They include species from serological groups A, B, C and G. Group A *Streptococcus* bacteria (GAS; *Streptococcus pyogenes*) are accountable for most cases of illness and can result in non-invasive disease such as pharyngitis, scarlet fever, impetigo, cellulitis or erysipelas, but some strains can lead to more severe invasive infections such as toxic shock syndrome, necrotizing fasciitis and septicemia. Additionally, complications of surface infections can result in immune-mediated sequelae. Lancefield's Group B *streptococcus* (GBS; *Streptococcus agalactiae*) is the predominant cause of neonatal sepsis in neonates and can cause pneumonia in elderly patients. Streptococcal groups C and G were initially recognized as animal pathogens but in recent years have been shown to have a strong potential for human disease. Illness generally presents itself similarly as in Group A *streptococcus* but has not been shown to lead to immune-mediated sequelae. Group C and G streptococci are often present in patients with underlying health problems, are of importance for elderly patients and are dispersed among several streptococcal species.

SUMMARY

In one aspect, the invention provides a novel polypeptide encoded by a Group C or Group G *Streptococcus* open reading frame number 554 (ORF 554). In one embodiment, the invention provides an isolated polypeptide that comprises an amino acid sequence set forth in SEQ ID NO:11, which is a consensus sequence of the novel several various ORF 554 sequences obtained from *Streptococcus dysgalactiae* subsp. *Equisimilis*, i.e., SEQ ID NO:2, SEQ ID NO:8, SEQ ID NO:10, SEQ ID NO:26 and SEQ ID NO:28; *Streptococcus constellatus* subsp. *Constellatus*, i.e., SEQ ID NO:4 and SEQ ID NO:32; *Streptococcus anginosus*, i.e., SEQ ID NO:6 and SEQ ID NO:30; or a fragment thereof. In some embodiments, the isolated polypeptide comprises or consists of an amino acid sequence set forth in SEQ ID NO: 2, SEQ ID NO:4, SEQ ID NO:6, SEQ ID NO:8, SEQ ID NO:10, SEQ ID NO:26, SEQ ID NO: 28, SEQ ID NO:30 and/or SEQ ID NO:32; or fragments thereof. In some embodiments, the isolated polypeptide has peptidyl-prolyl isomerase (PPI) activity.

In another aspect, the invention provides an isolated polypeptide that comprises or consists of an amino acid sequence that is at least 90%, 95% or 99% identical to SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and/or SEQ ID NO:32. In some embodiments, the isolated polypeptide has peptidyl-prolyl isomerase activity.

In another aspect, the invention provides isolated polynucleotides that encode a streptococcal ORF 554 polypeptide or a fragment thereof. In one embodiment, the invention provides an isolated polynucleotide that encodes a polypeptide comprising the amino acid sequence set forth in SEQ ID NO:11 or a fragment thereof. In some embodiments, the isolated polynucleotide encodes a polypeptide comprising or consisting of the amino acid sequence set forth in any one or more of SEQ ID NO:2, SEQ ID NO:4, SEQ ID NO:6, SEQ ID NO:8, SEQ ID NO:10, SEQ ID NO:26, SEQ ID NO: 28, SEQ ID NO:30 and SEQ ID NO:32, or fragments thereof. In some embodiments, the isolated polynucleotide comprises or consists of the nucleotide sequence set forth in any one or more of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31, or fragments thereof. In some embodiments, the polynucleotide is operably linked to a regulatory element.

In another aspect, the invention provides isolated polynucleotides that encode a polypeptide (or a fragment thereof) comprising or consisting of an amino acid sequence that is at least 90%, 95% or 99% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. In some embodiments, the isolated polypeptide has peptidyl-prolyl isomerase activity. In other embodiments, the isolated polynucleotide comprises or consists of a nucleotide sequence that is at least 90%, 95% or 99% identical to any one or more of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31, or fragments thereof. In some embodiments, the polynucleotide is operably linked to a regulatory element. In some embodiments, the regulatory element comprises an inducible promoter and/or a constitutive promoter.

In another aspect, the invention provides a polynucleotide vector comprising a nucleotide sequence that encodes a polypeptide comprising or consisting of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32, or fragments thereof. In some embodiments, the isolated polypeptide has peptidyl-prolyl isomerase activity. The vector can be e.g. a plasmid vector, a viral vector or the like. In other embodiments, the polynucleotide vector comprises a nucleotide sequence (or a fragment thereof) that is at least 90%, 95% or 99% identical to, or 100% identical to any one or more of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31. In some embodiments, the polynucleotide vector is an expression vector, which enables the production of a recombinant streptococcal PPI protein.

In another aspect, the invention provides an ex vivo cell comprising an isolated polynucleotide that comprises or consists of a nucleotide sequence, or a fragment thereof, that encodes a Group C or Group G Streptococcal PPI encoded by an ORF 554. In some embodiments the Group C or Group G Streptococcal PPI is encoded by an ORF 554 comprises or consists of an amino acid sequence, or a fragment thereof, that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. In some embodiments, the isolated polynucleotide comprises or consists of a nucleotide sequence, or a fragment thereof, that is at least 90%, 95% or 99% identical to, or 100% identical to any one or more of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31. In some embodiments, the cell produces a Group C or Group G Streptococcal PPI or a fragment thereof. In some embodiments, the host cell comprises a polynucleotide vector comprising an isolated polynucleotide comprising a regulatory sequence operably linked to the isolated polynucleotide. In some embodiments, the host cell comprises a polynucleotide vector comprising a regulatory element, which may be a constitutive or inducible promoter. In some embodiments, the host cell comprises a polynucleotide vector that is a plasmid, a viral vector or an expression vector. In some embodiments the host cell is selected from a bacterium, a mammalian cell, an insect cell or a yeast cell.

In another aspect, the invention provides an immunogenic composition useful in eliciting an immune response in a subject to a Group C or Group G Streptococcal PPI polypeptide. In some embodiments, the immunogenic composition comprises or consists of a polypeptide, or fragment thereof, that comprises or consists of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. In other embodiments, the immunogenic composition comprises or consists of an isolated polynucleotide, or fragment thereof, that comprises or consists of a nucleotide sequence that is at least 90%, 95% or 99% identical to, or 100% identical to any one or more of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31. In some embodiments, the polynucleotide further comprises a regulatory element, such as e.g. an inducible or constitutive promoter that regulates the expression of the isolated polynucleotide in the subject.

In another aspect, the invention provides an immunological reagent comprising or consisting of an epitope binding region which binds to a streptococcal PPI encodes by a Group C or Group G Streptococcal ORF 554. In some embodiments, the immunological reagent comprises or consists of an antibody that specifically binds to at least one streptococcal PPI polypeptide encoded by ORF 554. In some embodiments, the antibody binds a polypeptide comprising or consisting of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. The antibody may be a monoclonal antibody or a polyclonal antibody. In some embodiments, the antibody is a chimeric antibody, including e.g. a humanized antibody.

In another aspect, the invention provides a method for inducing an immune response in a subject to a beta hemolytic *streptococcus* or beta hemolytic streptococcal infection, comprising administering to the subject an immunogenic composition comprising a Group C or Group G Streptococcal PPI protein or a fragment thereof. In some embodiments, the PPI protein comprises or consists of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32.

In another aspect, the invention provides a method for inducing an immune response in a subject to a beta hemolytic *streptococcus* or beta hemolytic streptococcal infection, comprising administering to the subject an immunogenic composition comprising a polynucleotide that encodes a Group C or Group G Streptococcal PPI protein or a fragment thereof. In some embodiments, the PPI protein comprises or consists of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. In other embodiments, the polynucleotide comprises or consists of a nucleotide sequence that is at least 90%, 95% or 99% identical to, or 100% identical to any one or more of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31. In some embodiments, the polynucleotide further comprises a regulatory element, such as e.g. an inducible or constitutive promoter that regulates expression of the isolated polynucleotide in the subject.

In another aspect, the invention provides the use of an isolated Group C or Group G Streptococcal PPI polypeptide, or a fragment thereof, in the manufacture of a medicament useful in the prophylactic treatment of a beta hemolytic streptococcal infection in a subject. In some embodiments, the subject is a human. In some embodiments, the PPI polypeptide comprises or consists of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32.

In another aspect, the invention provides the use of an isolated polynucleotide that encodes a Group C or Group G Streptococcal PPI polypeptide, or a fragment thereof, in the manufacture of a medicament useful in the prophylactic treatment of a beta hemolytic streptococcal infection in a subject. In some embodiments, the subject is a human patient. In some embodiments, the PPI polypeptide comprises or consists of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. In other embodiments, the polynucleotide comprises or consists of a nucleotide sequence that is at least 90%, 95% or 99% identical to, or 100% identical to any one or more of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31. In some embodiments, the polynucleotide further comprises a regulatory element, such as e.g. an inducible or constitutive promoter that enables expression of the isolated polynucleotide in the subject.

In another aspect, the invention provides the use of an immunological reagent, which comprises a region that specifically binds to an epitope of a Group C or Group G Streptococcal PPI polypeptide, in the manufacture of a medicament useful in the prophylactic treatment of a beta hemolytic streptococcal infection in a subject. In some embodiments, the immunological reagent comprises or consists of an antibody. In some embodiments, the subject is a human patient. In some embodiments, the PPI polypeptide comprises or consists of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. In some embodiments, the antibody may be a monoclonal antibody or a polyclonal antibody. In some embodiments, the antibody may be a chimeric antibody, such as e.g. a humanized antibody or a polyclonal antibody.

In another aspect, the invention provides a method for treating a beta hemolytic streptococcal infection in a subject comprising administering a therapeutically effective amount of an antibody, or a fragment thereof, which specifically binds to an epitope of a Group C or Group G Streptococcal PPI polypeptide, in a pharmaceutically effective excipient. In some embodiments, the subject is a human. In some embodiments, the PPI polypeptide comprises or consists of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. In some embodiments, the antibody may be a monoclonal antibody or a polyclonal antibody. In some embodiments, the antibody may be a chimeric antibody, such as e.g. a humanized antibody or a polyclonal antibody.

In yet other aspects, the invention provides kits comprising (a) an isolated Group C or Group G Streptococcal PPI polypeptide, having an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32; (b) an isolated polynucleotide that encodes a Group C or Group G Streptococcal PPI polypeptide (supra); and/or (c) an antibody that specifically binds to an epitope of a Group C or Group G Streptococcal PPI polypeptide (supra).

BRIEF DESCRIPTION OF THE SEQUENCE LISTING

SEQ ID NO:1 is the nucleotide sequence of ORF 554 in *Streptococcus dysgalactiae* subsp. *Equisimilis*.

SEQ ID NO:2 is the amino acid sequence encoded by ORF 554 in *Streptococcus dysgalactiae* subsp. *Equisimilis*.

SEQ ID NO:3 is the nucleotide sequence of ORF 554 in *Streptococcus constellatus* subsp. *Constellatus*.

SEQ ID NO:4 is the amino acid sequence encoded by ORF 554 in *Streptococcus constellatus* subsp. *Constellatus*.

SEQ ID NO:5 is the nucleotide sequence of ORF 554 in *Streptococcus anginosus*.

SEQ ID NO:6 is the amino acid sequence encoded by ORF 554 in *Streptococcus anginosus*.

SEQ ID NO:7 is the nucleotide sequence of ORF 554 in *Streptococcus sp.* strain N04A27.

SEQ ID NO:8 is the amino acid sequence encoded by ORF 554 in *Streptococcus sp.* strain N04A27.

SEQ ID NO:9 is the nucleotide sequence of ORF 554 in *Streptococcus sp.* strain N04AFT.

SEQ ID NO:10 is the amino acid sequence encoded by ORF 554 in *Streptococcus sp.* strain N04AFT.

SEQ ID NO:11 is the consensus amino acid sequence of the polypeptides of SEQ ID NO:2, SEQ ID NO:4, SEQ ID NO:6, SEQ ID NO:8 and SEQ ID NO:10.

SEQ ID NO:12 is the nucleotide sequence of ORF 554 of *S. agalactiae*, GBS0827.

SEQ ID NO:13 is the amino acid sequence encoded by ORF 554 of *S. agalactiae*, GBS0827.

SEQ ID NO:14 is the nucleotide sequence of ORF 554 of *S. pyogenes*, SPY_1390.

SEQ ID NO:15 is the amino acid sequence encoded by ORF 554 of *S. pyogenes*, SPY_1390.

SEQ ID NO:16 is the nucleotide sequence of ORF 554 of *S. zoopedimicus*.

SEQ ID NO:17 is the amino acid sequence encoded by ORF 554 of *S. zoopedimicus*.

SEQ ID NO:18 is the nucleotide sequence of primer D554 F1.

SEQ ID NO:19 is the amino acid sequence of primer D554 F2.

SEQ ID NO:20 is the nucleotide sequence of primer D554 F5.

SEQ ID NO:21 is the amino acid sequence of primer D554 R1.

SEQ ID NO:22 is the nucleotide sequence of primer D554 R4.

SEQ ID NO:23 is the nucleotide sequence of primer ATCC12394 554 F.

SEQ ID NO:24 is the amino acid sequence of primer ATCC12394 554 R.

SEQ ID NO:25 is the nucleotide sequence of ORF 554 in *Streptococcus dysgalactiae* subsp. *equisimilis*.

SEQ ID NO:26 is the amino acid sequence encoded by ORF 554 in *Streptococcus dysgalactiae* subsp. *equisimilis*.

SEQ ID NO:27 is the nucleotide sequence of ORF 554 in *Streptococcus dysgalactiae* subsp. *equisimilis*.

SEQ ID NO:28 is the amino acid sequence encoded by ORF 554 in *Streptococcus dysgalactiae* subsp. *equisimilis*.

SEQ ID NO:29 is the nucleotide sequence of ORF 554 in *Streptococcus anginosus*.

SEQ ID NO:30 is the amino acid sequence encoded by ORF 554 in *Streptococcus anginosus*.

SEQ ID NO:31 is the nucleotide sequence of ORF 554 in *Streptococcus constellatus* subsp. *constellatus*.

SEQ ID NO:32 is the amino acid sequence encoded by ORF 554 in *Streptococcus constellatus* subsp. *constellatus*.

DETAILED DESCRIPTION

The invention describes polypeptides and polynucleotides obtained from Group C or Group G *Streptococcus* species, which correspond to *Streptococcus pyogenes* open reading frame 554 (ORF 554). DNA and amino acid sequences for ORF 554 are provided in published International patent application number WO 02/083859. These ORF 554 polypeptides are similar to the *Streptococcus pyogenes* peptidyl-prolyl isomerase (PPI) protein. These polynucleotides and polypeptides may be used in immunogenic compositions to induce an immune response to beta hemolytic *streptococcus* or beta hemolytic streptococcal infection in a subject.

The terms "polynucleotide", "nucleic acid" and "nucleic acid fragment" are used interchangeably herein. These terms encompass nucleotides connected by phosphodiester linkages. A "polynucleotide" may be a ribonucleic acid (RNA) or deoxyribonucleic acid (DNA) polymer that is single- or double-stranded, that optionally contains synthetic, non-natural or altered nucleotide bases. A polynucleotide in the form of a polymer of DNA may comprise one or more segments of cDNA, genomic DNA, synthetic DNA, or mixtures thereof. Nucleotide bases are indicated herein by a single letter code: adenine (A), guanine (G), thymine (T), cytosine (C), inosine (I) and uracil (U).

A "protein" or "polypeptide" is a chain of amino acids arranged in a specific order determined by the coding sequence in a polynucleotide encoding the polypeptide.

The term "isolated" means altered "by the hand of man" from the natural state. If a composition or substance occurs in nature, in order for it to be considered "isolated" it must have been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein. Isolated polynucleotides or isolated polypeptides may be purified from a host cell in which they naturally occur. Conventional nucleic acid purification methods known to those skilled in the art to which the invention is directed may be used to obtain isolated polynucleotides.

Group C or Group G Streptococcal ORF 554 Polynucleotides

The Group C or Group G streptococcal ORF 554 polynucleotides described herein may be obtained using standard cloning and screening techniques. These polynucleotides may be obtained, for example, from genomic DNA, from a cDNA library derived from mRNA, from a genomic DNA library, or can be synthesized using well known and commercially available techniques, such as e.g. by PCR from a cDNA library or via RT-PCR (reverse transcription-polymerase chain reaction).

The term "recombinant" means, for example, that a polynucleotide is made by an artificial combination of two or more otherwise separated polynucleotide segments, e.g., by chemical synthesis or by the manipulation of isolated polynucleotides using genetic engineering techniques. A "recombinant DNA construct" comprises any of the isolated polynucleotides of the present invention operably linked to at least one regulatory element.

In one aspect, the invention provides isolated polynucleotides, or fragments thereof, that encode a Group C or Group G *Streptococcus* prolyl-peptidyl isomerase (PPI) protein.

In one embodiment, an isolated polynucleotide encodes a polypeptide that comprises the amino acid sequence set forth in SEQ ID NO:11. The amino acid sequence of SEQ ID NO:11 is the consensus sequence obtained after aligning the polypeptide sequences obtained from the conceptual translation of ORF 554 of the Group C or Group G species *Streptococcus dysgalactiae* subsp. *Equisimilis*, represented by SEQ ID NO:2, SEQ ID NO:4, SEQ ID NO:6, SEQ ID NO:8 and SEQ ID NO:10.

In one embodiment, the invention provides an isolated polynucleotide encoding any one or more polypeptide comprising SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 or SEQ ID NO:32, or fragments thereof. Exemplary nucleotide sequences are set forth in SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31. In another embodiment, the invention provides polynucleotides that differ from the polynucleotide sequences shown in SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31 due to degeneracy of the genetic code. These polynucleotides encode the same ORF 554 polypeptide.

Orthologues and allelic variants of the Group C or Group G Streptococcal ORF 554 polynucleotides can readily be identified using methods well known in the art. Allelic variants and orthologs of the ORF 554 polynucleotides can comprise a nucleotide sequence that is typically at least about 90-95% or more identical to any one or more of the nucleotide sequences shown in SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31, or fragments thereof. The allelic variants and orthologs of ORF 554 polynucleotides can encode a polypeptide that comprises an amino acid sequence that is at least 90% identical to the amino acid sequence set forth in any one or more of SEQ ID NO: 2, SEQ ID NO:4, SEQ ID NO:6, SEQ ID NO:8, SEQ ID NO:10, SEQ ID NO:26, SEQ ID NO: 28, SEQ ID NO:30 and SEQ ID NO:32. Such polynucleotides can readily be identified as being able to hybridize under stringent conditions, to any one or more of the polynucleotides having a nucleotide sequence set forth in SEQ ID NO:1, SEQ ID NO:3, SEQ ID NO:5, SEQ ID NO:7, SEQ ID NO:9, SEQ ID NO:25, SEQ ID NO:27, SEQ ID NO:29 and/or SEQ ID NO:31, or fragments thereof.

Moreover, the allelic variants and orthologues of ORF 554 polynucleotides can comprise only a fragment of the coding region of a Group C or Group G Streptococcal ORF 554 polynucleotide, such as a fragment of a polynucleotide set forth in SEQ ID NO:1, SEQ ID NO:3, SEQ ID NO:5, SEQ ID NO:7, SEQ ID NO:9, SEQ ID NO:25, SEQ ID NO:27, SEQ ID NO:29 and/or SEQ ID NO:31, or a fragment of these nucleotide sequences. In certain embodiments, such fragments encode immunogenic fragments.

It is well understood by one skilled in the art that many levels of sequence identity are useful in identifying related polynucleotide and polypeptide sequences. Sequence alignments and percent identity calculations can be performed using the MEGALIGN™ program of the LASERGENE™ bioinformatics computing suite (DNASTAR Inc., Madison, Wis.). Multiple alignment of the sequences can be performed using the Clustal method of alignment (Higgins and Sharp, Gene, 73(1):237-44, 1988) with the default parameters of e.g. GAP PENALTY=10 and GAP LENGTH PENALTY=10. Default parameters for pairwise alignments using the Clustal method can be e.g. KTUPLE 1, GAP PENALTY=3, WINDOW=5 and DIAGONALS SAVED=5.

The ORF 554 polynucleotides of the invention may be used for the production of recombinant polypeptides for inclusion in immunogenic compositions and other uses. For the production of recombinant polypeptides, the polynucleotide may include the coding sequence for the mature polypeptide, by itself, or the coding sequence for the mature polypeptide linked with other coding sequences, such as those encoding a leader or secretory sequence, a pre-, or pro- or prepro-protein sequence, or other fusion peptide portions. For example, a marker sequence which facilitates purification of the fused polypeptide can be linked to the coding sequence (see Gentz et al., Proc. Natl. Acad. Sci. USA, 86:821-824, 1989). The polynucleotide may also contain non-coding 5' and 3' sequences, such as transcribed, non-translated sequences, splicing and polyadenylation signals.

In certain embodiments, the polynucleotide sequence information provided herein allows for the preparation of relatively short DNA (or RNA) oligonucleotide sequences having the ability to specifically hybridize to nucleotide sequences of the selected polynucleotides disclosed herein. The term "oligonucleotide" as used herein is defined as a molecule comprising two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. Thus, in some embodiments, nucleic acid probes of an appropriate length are prepared based on a selected nucleotide sequence, e.g., a sequence such as that shown in SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31.

The ability of such nucleic acid probes to specifically hybridize to a polynucleotide encoding a Group C or Group G Streptococcal PPI polypeptide lends them particular utility in a variety of embodiments. In some embodiments, the probes can be used in a variety of assays for detecting the presence of complementary sequences in a given sample.

In some embodiments, the oligonucleotides may be used as primers. These primers may be generated in any manner, including chemical synthesis, DNA replication, reverse transcription, or a combination thereof. The sequence of such primers is designed using a polynucleotide described herein for use in detecting, amplifying or mutating a defined segment of an ORF 554 polynucleotide that encodes a Group C or Group G Streptococcal PPI polypeptide using polymerase chain reaction (PCR) technology.

In certain embodiments, it is advantageous to employ a polynucleotide described herein in combination with an appropriate label for detecting hybrid formation. A wide variety of appropriate labels are known in the art, including radioactive, enzymatic or other ligands, such as avidin/biotin, which are capable of giving a detectable signal.

Polynucleotides which are identical or sufficiently identical to a nucleotide sequence contained in one of SEQ ID NO:1, SEQ ID NO:3, SEQ ID NO:5, SEQ ID NO:7, SEQ ID NO:9, SEQ ID NO:12, SEQ ID NO:14, SEQ ID NO:16 and SEQ ID NO:18 through SEQ ID NO:24, SEQ ID NO:25, SEQ ID NO:27, SEQ ID NO:29 and SEQ ID NO:31, or a fragment thereof, may be used as hybridization probes for cDNA and genomic DNA, or as primers for a nucleic acid amplification (PCR) reaction, to isolate full-length cDNAs and genomic clones encoding polypeptides described herein and to isolate cDNA and genomic clones of other genes (including genes encoding homologs and orthologs from species other than *Streptococcus dysgalactiae*) that have a high sequence similarity to the polynucleotide sequences set forth in of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31, or a fragment thereof. Typically these nucleotide sequences are from at least about 90% identical to at least about 99% identical to that of the reference polynucleotide sequence. The probes or primers will generally comprise at least 15 nucleotides, at least 30 nucleotides or at least 50 nucleotides.

There are several methods available and well known to those skilled in the art to obtain full-length cDNAs or to extend short cDNAs, such as e.g. those based on the method of rapid amplification of cDNA ends (RACE). See Frohman et al., Proc. Natl. Acad. Sci. USA 85, 8998-9002, 1988. Recent modifications of the technique, exemplified by the MARATHON™ technology (Clontech Laboratories Inc.) for example, have significantly simplified the search for longer cDNAs. In the MARATHON™ technology, cDNAs have been prepared from mRNA extracted from a chosen tissue and an "adaptor" sequence ligated onto each end. Nucleic acid amplification (PCR) is then carried out to amplify the "missing" 5' end of the cDNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or by carrying out a separate full-length PCR using the new sequence information for the design of the 5' primer.

Group C or Group G Streptococcal PPI Polypeptides

In one aspect, the present invention provides isolated Group C or Group G Streptococcal peptidyl-prolyl isomerase (PPI) polypeptides (encoded by ORF 554), which can be used, inter alia, as an immunogen and in immunogenic compositions. The PPI polypeptide may be a recombinant polypeptide.

In one embodiment, the invention provides an isolated polypeptide that comprises the amino acid sequence set forth in SEQ ID NO:11. The amino acid sequence set forth in SEQ ID NO:11 is the consensus sequence obtained after aligning the polynucleotide sequences obtained for ORF 554 of *Streptococcus dysgalactiae* subsp. *Equisimilis*, and set forth in SEQ ID NO:2, SEQ ID NO:4, SEQ ID NO:6, SEQ ID NO:8 and SEQ ID NO:10.

In one embodiment, the polypeptide comprises an amino acid sequence that is at least 90%, 95%, or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32; functional and non-functional naturally occurring variants or biological equivalents of said polypeptides; recombinantly produced variants or biological equivalents of said polypeptides; orthologs and/or allelic variants of said polypeptides; and fragments of said polypeptides.

Biological equivalents or variants of Group C or Group G Streptococcal PPI polypeptides include both functional and non-functional polypeptides. Functional biological equivalents or variants include naturally occurring amino acid sequence variants of a polypeptide, which maintains the ability to elicit an immunological or antigenic response in a subject. Functional variants typically contain conservative substitutions of one or more amino acids of one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32; or substitutions, deletions or insertions of non-critical residues in non-critical regions of the polypeptide.

In some embodiments, modifications and changes can be made in the structure of the PPI polypeptide and still obtain a PPI polypeptide having the same antigenicity as an unchanged Group C or Group G Streptococcal PPI polypeptide. For example, certain amino acids can be substituted for other amino acids in a sequence without appreciable loss of antigenicity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such modifications and changes, the hydropathic index of amino acids can be considered. The importance of the hydropathic amino acid index in conferring interactive biologic function on a polypeptide is generally understood in the art (Kyte and Doolittle, J Mol Biol, 157: p. 105-132, 1982). It is known in the art that certain amino acids can be substituted for other amino acids having a similar hydropathic index or score and still result in a polypeptide having similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is generally accepted in the art that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In some embodiments, the modified or changed PPI polypeptide comprises one or more substituted amino acids whose hydropathic indices are within ±2 of each original amino acid. In other embodiments, the hydropathic index of each substituted amino acid is within ±1 of its original amino acid. In yet other embodiments, the hydropathic index of each substituted amino acid is within ±0.5 of its original amino acid.

Substitution of like amino acids can also be made on the basis of hydrophilicity, particularly where the biological functional equivalent polypeptide or peptide thereby created is intended for use in immunological embodiments. U.S. Pat. No. 4,554,101 teaches that the greatest local average hydrophilicity of a polypeptide, as governed by the hydrophilicity of its adjacent amino acids, correlates with its immunogenicity and antigenicity.

"Variant," as the term is used herein, is a polynucleotide or polypeptide that differs from a reference polynucleotide or polypeptide respectively, but retains some essential property. A typical variant of a polynucleotide differs in nucleotide sequence from a reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from a reference polypeptide. Generally, differences are limited so that the sequences of the reference polypeptide and the variant polypeptide are similar overall and, in many regions, identical. A variant polypeptide and its reference polypeptide may differ in amino acid sequence by one or more substitutions, additions and deletions in any combination. A substituted or inserted amino acid residue may or may not be one encoded by the genetic code. A variant of a polynucleotide or polypeptide may be naturally occurring such as an allelic variant, or it may be a variant that is not known to occur naturally. Non-naturally occurring variants of polynucleotides and polypeptides may be made by mutagenesis techniques or by direct synthesis.

Recombinant Systems

For the recombinant production of polypeptides, host cells can be genetically engineered to incorporate expression systems comprising ORF 554 polynucleotides of the invention. Polynucleotides can be introduced into host cells e.g. by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd ed., Cold Spring Harbor Laboratory Press, Cold Spring Harbor, N.Y. (1989.) Those methods include e.g. calcium phosphate transfection, DEAE-dextran mediated transfection, transvection, microinjection, ultrasound, cationic lipid-mediated transfection, electroporation, transduction, scrape loading, ballistic introduction and infection.

Representative examples of suitable host cells include bacterial cells (e.g., streptococci, staphylococci, *E. coli, Streptomyces spp.* and *Bacillus subtilis* cells), yeast cells (e.g., *Pichia* and *Saccharomyces*), mammalian cells (e.g. CHO cells), and insect cells (e.g., Sf9 and Sf21).

The recombinantly produced polypeptides may be recovered and purified from recombinant cell cultures by well-known methods, including high performance liquid chromatography, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography.

Any one or more of myriad vector systems may be used to express and produce of Group C or Group G Streptococcal PPI polypeptides in a heterologous cell system. Such vector systems include, among others, chromosomal, episomal and virus-derived systems, e.g., vectors derived from bacterial plasmids, attenuated bacteria such as *Salmonella* (U.S. Pat. No. 4,837,151) from bacteriophage, from transposons, from yeast episomes, from insertion elements, from yeast chromosomal elements, from viruses such as vaccinia and other poxviruses, sindbis, adenovirus, baculoviruses, papova viruses, such as SV40, fowl pox viruses, pseudorabies viruses and retroviruses, alphaviruses such as Venezuelan equine encephalitis virus (U.S. Pat. No. 5,643,576), nonsegmented negative-stranded RNA viruses such as vesicular stomatitis virus (U.S. Pat. No. 6,168,943), and vectors derived from combinations thereof, such as those derived from plasmid and bacteriophage genetic elements, such as cosmids and phagemids. The expression systems should include control regions that regulate as well as engender expression, such as promoters and other regulatory elements (such as a polyadenylation signal). Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

In one embodiment, the present invention provides expression vectors comprising Group C or Group G Streptococcal ORF 554 polynucleotides encoding a Group C or Group G Streptococcal PPI polypeptide. The expression vectors comprise ORF 554 polynucleotides that encode polypeptides comprising or consisting of an amino acid sequence that is at least 90%, 95% or 99% identical to, or 100% identical to any one or more of SEQ ID NO: 2, SEQ ID NO:4, SEQ ID NO:6, SEQ ID NO:8, SEQ ID NO:10, SEQ ID NO:11, SEQ ID NO:26, SEQ ID NO: 28, SEQ ID NO:30 and SEQ ID NO:32. Alternatively, the expression vectors comprise a polynucleotide comprising or consisting of a nucleotide sequence that is at least 90%, 95% or 99% identical to, or 100% identical to any one or more of SEQ ID NO:1, SEQ ID NO:3, SEQ ID NO:5, SEQ ID NO:7, SEQ ID NO:9, SEQ ID NO:25, SEQ ID NO:27, SEQ ID NO:29 and SEQ ID NO:31. In other embodiments, the expression vectors of the invention comprise a polynucleotide operatively linked to an enhancer-promoter. In still other embodiments, the expression vectors comprise a polynucleotide operatively linked to a prokaryotic promoter. Alternatively, the expression vectors comprise a polynucleotide operatively linked to an enhancer-promoter that is a eukaryotic promoter. The expression vectors further comprise a polyadenylation signal that is positioned 3' of the carboxy-terminal amino acid and within a transcriptional unit of the encoded polypeptide.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are enhancers, silencers, splicing signals, polyadenylation signals, termination signals, RNA export elements, internal ribosome entry sites et cetera.

As used herein, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" or "operably linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter a/ia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct described herein can be any enhancer-promoter that drives expression in a cell to be transfected. By employing an enhancer-promoter with well-known properties, the level and pattern of gene product expression can be optimized. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., "Molecular Cloning: A Laboratory Manual" 2nd, ed, Cold Spring Harbor Laboratory, Cold Spring Harbor Laboratory Press, Cold Spring Harbor, N.Y., 1989, incorporated herein by reference.

In another embodiment, the expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., Genes Dev, 1: p. 268-277, 1987), lymphoid-specific promoters (Calame and Eaton, Adv Immunol, 43: p. 235-275, 1988), promoters of T cell receptors (Winoto and Baltimore, EMBO J, 8: p. 729-733, 1989) and immunoglobulins (Banerji et al., Cell, 33: p. 729-740, 1983), (Queen and Baltimore, Cell, 33: p. 741-748, 1983), neuron-specific promoters (e.g., the neurofilament promoter; Byrne and Ruddle, PNAS, 86: p. 5473-5477, 1989), pancreas-specific promoters (Edlund et al., Science, 230: p. 912-916, 1985), and mammary gland-specific promoters (e.g., milk whey promoter; U.S. Pat. No. 4,873,316 and International Application EP 264,166). In another embodiment, regulatory elements include developmentally-regulated promoters, such as e.g. the murine hox promoters (Kessel and Gruss, Science, 249: p. 374-379, 1990) and the a-fetoprotein promoter (Campes and Tilghman, Genes Dev, 3: p. 537-546, 1989).

Vector DNA can be introduced into prokaryotic or eukaryotic cells via conventional transformation, infection or transfection techniques. As used herein, the terms "transformation" and "transfection" are intended to refer to a variety of art-recognized techniques for introducing foreign nucleic acids into a host cell, which includes e.g. calcium phosphate or calcium chloride co-precipitation, DEAE-dextran-mediated transfection, lipofection, ultrasound and electroporation methods. Suitable methods for transforming or transfecting host cells can be found in Sambrook, et al. ("Molecular Cloning: A Laboratory Manual" 2nd, ed, Cold Spring Harbor Laboratory, Cold Spring Harbor Laboratory Press, Cold Spring Harbor, N.Y., 1989), and other laboratory manuals.

The production of polypeptides in prokaryotes is most often carried out in *E. coli* with vectors containing constitutive or inducible promoters directing the expression of either fusion or non-fusion proteins Constitutive promoters include, for example, lambda PL, spc ribosomal and beta-lactamase. Inducible promoters include, for example, arabinose, lac, tac and maltose binding protein. Fusion vectors add a number of amino acids to a protein encoded therein, usually to the amino terminus of the recombinant protein. Such fusion vectors typically serve three purposes: to increase expression of recombinant protein; to increase the solubility of the recombinant protein; and to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. The invention also provides vectors (e.g., expression vectors, sequencing vectors, cloning vectors) which comprise at least one polynucleotide of the invention, host cells which are genetically engineered with vectors of the invention, and production of polypeptides of the invention by recombinant techniques. Cell-free translation systems can also be employed to produce such proteins using RNAs derived from the DNA constructs of the invention.

Group C or Group G Streptococcal PPI Antibodies

The polypeptides of the invention, including those comprising the amino acid sequences set forth in SEQ ID NO:2, SEQ ID NO:4, SEQ ID NO:6, SEQ ID NO:8, SEQ ID NO:10, or SEQ ID NO:11, fragments and analogs thereof, or cells expressing said sequences, fragments and/or analogs, can also be used as immunogens to produce antibodies that specifically bind to the polypeptides of the invention. In one aspect, the invention provides (a) antibodies that specifically bind to a Group C or Group G Streptococcal PPI polypeptide, (b) the use of such antibodies to detect the presence of, or measure the quantity or concentration of streptococcal PPI polypeptides in a cell, a cell or tissue extract, or a biological fluid and (c) the use of such antibodies for treatment of beta hemolytic streptococcal infection in a subject.

The antibodies of the invention include polyclonal antibodies, monoclonal antibodies, chimeric antibodies, and anti-idiotypic antibodies. Polyclonal antibodies are heterogeneous populations of antibody molecules derived from the sera of animals immunized with an antigen. Monoclonal antibodies are a substantially homogeneous population of antibodies that bind to specific antigens. In general, antibodies can be made, for example, using traditional hybridoma techniques (Kohler and Milstein (1975) Nature, 256: 495-499), recombinant DNA methods (U.S. Pat. No. 4,816,567), or phage display using antibody libraries (Clackson et al. (1991) Nature, 352: 624-628; Marks et al. (1991) J. Mol. Biol., 222: 581-597). For additional antibody production techniques, see Antibodies: A Laboratory Manual, eds. Harlow and Lane, Cold Spring Harbor Laboratory, 1988. The present invention is not limited to any particular source, method of production, or other special characteristics of an antibody.

Other suitable methods of producing or isolating antibodies that specifically bind to a Group C or Group G streptococcal PPI polypeptide epitope can be used. In some embodiments, the recombinant antibody is selected from a peptide or protein display library such as e.g. a bacteriophage, ribosome, oligonucleotide, RNA and cDNA display libraries (EP368, 684; PCT/GB91/01134; PCT/GB92/01755; PCT/GB92/002240; PCT/GB92/00883; PCT/GB93/00605; PCT/GB94/01422; PCT/GB94/02662; PCT/GB97/01 835; WO90/14443; WO90/14424; WO90/14430; PCT/US94/1234; WO92/18619; WO96/07754; EP614,989; WO95/16027; WO88/06630; WO90/3809; U.S. Pat. No. 4,704,692; PCT/US91/02989; WO89/06283; EP371,998; EP550,400; EP229, 046; and PCT/US91/07149.) In other embodiments, the recombinant antibody is selected from a library of stochastically generated peptides or proteins (U.S. Pat. Nos. 5,723, 323; 5,763,192; 5,814,476; 5,817,483; 5,824,514; 5,976,862; WO 86/05803; and EP 590,689.) In yet other embodiments, the recombinant antibody is produced in a transgenic animal that is capable of producing a repertoire of human antibodies (Nguyen et al., Microbiol. Immunol. 41:901-907, 1997; Sandhu et al., Crit. Rev. Biotechnol. 16:95-118, 1996; and Eren et al., Immunol. 93:154-161, 1998.) Other techniques for producing recombinant antibodies include e.g. (a) single cell antibody producing technologies such as the selected lymphocyte antibody method ("SLAM") (U.S. Pat. No. 5,627,052), (b) gel microdroplet and flow cytometry methods (Powell et al., Biotechnol. 8:333-337, 1990), and (c) B-cell selection (Steenbakkers et al., Molec. Biol. Reports 19:125-134, 1994). These same methods can also be deployed to improve the affinity and/or avidity of an anti-Group C or Group G streptococcal PPI antibody to its specific binding target.

Intact antibodies are immunoglobulins (Ig), and they typically are tetrameric glycosylated proteins composed of two light chains (~25 kDa each) and two heavy chains (~50 kDa each). Light chains are classified into two isotypes (A and K), and heavy chains are classified into five isotypes (A, D, E, G, and M). Some heavy chain isotypes are further divided into isotype subclasses, e.g., $IgG_1$, $IgG_2$, $IgG_3$, and $IgG_4$.

The domain and three dimensional structures of different antibodies are known in the art (Harlow and Lane, supra). In brief, the light chain is composed of a constant domain ($C_L$) and an N-terminal variable domain ($V_L$). The heavy chain is composed of three or four constant domains ($C_H$), a hinge region, and a N-terminal variable domain ($V_H$). The $C_H$ adjacent to the $V_H$ domain is designated $C_{H1}$. The $V_H$ and $V_L$ domains contain four regions of conserved sequence called framework (FR) regions (FR1, FR2, FR3, and FR4), which form a scaffold for three regions of hypervariable sequence called complementarity determining regions (CDR). The CDRs (CDR1, CDR2, and CDR3) contain most of the antibody amino acids that specifically recognize and bind antigen. Heavy chain CDRs are denoted H1, H2, and H3, while light chain CDRs are denoted L1, L2, and L3.

The Fab fragment (Fragment antigen-binding) consists of $V_H$—$C_{H1}$ and $V_L$—$C_L$ domains covalently linked by a disulfide bond between the constant regions. The $F_v$ fragment is smaller and consists of $V_H$ and $V_L$ domains non-covalently linked. To overcome the tendency of non-covalently domains to dissociate, a single chain $F_v$ fragment ($scF_v$) can be constructed. The $scF_v$ contains a flexible polypeptide that links the (a) C-terminus of $V_H$ to the N-terminus of $V_L$, or the (b) C-terminus of $V_L$ to the N-terminus of $V_H$. A 15-mer $(Gly_4Ser)_3$ peptide may be used as a linker, but other linkers are known in the art.

Antibody diversity is created by use of multiple germline genes encoding variable regions and a variety of somatic events. The somatic events include recombination of variable gene segments and diversity (D) and joining (J) gene segments to make a complete $V_H$ region and the recombination of variable and joining gene segments to make a complete $V_L$ region. CDR3 (H3) is the greatest source of molecular diversity within an antibody sequence. H3, for example, can be as short as two amino acid residues or greater than 26. The smallest antigen-binding fragment is the Fv, which consists of the $V_H$ and the $V_L$ domains.

Anti-Group C or Group G streptococcal PPI antibodies of this invention may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Antibody isotype such as $IgG_1$, $IgG_2$, $IgG_3$ or $IgG_4$ is determined by the $CH_2$ and $CH_3$ domains. Isotypes may be switched by changing these domains without affecting antigen binding. Constant regions are known in the art (see, for example, Kabat et al., Sequences of Proteins of Immunological Interest, No. 91-3242, National Institutes of Health Publications, Bethesda, Md., 1991.)

The term "antibody" is also meant to include both intact molecules as well as fragments such as Fab, which are capable of binding antigen. Fab fragments lack the Fc fragment of intact antibody, clear more rapidly from the circulation, and may have less non-specific tissue binding than an intact antibody (Wahl et al., 1983, J. Nucl. Med. 24:316-325). It will be appreciated that Fab and other fragments of the antibodies useful in the present invention may be used for the detection and quantitation of Group C or Group G Streptococcal PPI polypeptides according to the methods for intact antibody molecules.

Chimeric antibodies are molecules, different portions of which are derived from different animal species, such as those having variable region ($V_H$, $V_L$) derived from a murine monoclonal antibody and a human immunoglobulin constant region ($CH_1$—$CH_2$—$CH_3$, $C_L$). Chimeric antibodies and methods for their production are known in the art (Cabilly et al., 1984, Proc. Natl. Acad. Sci. USA 81:3273-3277; Morrison et al., 1984, Proc. Natl. Acad. Sci. USA 81:6851-6855; Boulianne et al., 1984, Nature 312:643-646; Cabilly et al., European Patent Application 125023 (published Nov. 14, 1984); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Morrison et al., European Patent Application 173494 (published Mar. 5, 1986); Sahagan et al., 1986, J. Immunol. 137:1066-1074; Robinson et al., PCT/US86/02269 (published May 7, 1987); Liu et al., 1987, Proc. Natl. Acad. Sci. USA 84:3439-3443; Sun et al., 1987, Proc. Natl. Acad. Sci. USA 84:214-218; Better et al., 1988, Science 240:1041-1043). These references are hereby incorporated by reference.

The antibodies are used in a variety of ways, e.g., for confirmation that a protein is expressed, or to confirm where a protein is expressed. Labeled antibody (e.g., fluorescent labeling for FACS) can be incubated with intact bacteria and the presence of the label on the bacterial surface confirms the location of the protein, for instance.

Immunogenic Compositions

The present invention provides immunogenic compositions comprising one or more of Group C or Group G streptococcal PPI polypeptides. In some embodiments, the immunogenic compositions comprise one or more PPI polypeptides comprising an amino acid residue sequence that is at least 90%, 95%, 99% or 100% identical to SEQ ID NOs: 2, 4, 6, 8 and 10, and one or more physiologically acceptable carriers.

In other embodiments, the immunogenic compositions of the invention comprise polynucleotides that encode a Group C or Group G streptococcal PPI polypeptide, and one or more physiologically acceptable carriers. In some embodiments, the immunogenic compositions comprise polynucleotides having a nucleotide sequence that is at least 90%, 95%, 99% or 100% identical to one or more of SEQ ID NOs: 1, 3, 5, 7 and/or 9.

The term "immunogenic composition" as used herein refers to any type of biological agent in an administratable form capable of stimulating an immune response in a subject inoculated with the immunogenic composition. An immune response may include induction of antibodies and/or induction of a T-cell response. The term "protection," when used in reference to an immunogenic composition, refers herein to the amelioration (either partial or complete) of any of the symptoms associated with the disease or condition in question. Thus, protection of subjects from infection by a *Streptococcus* species such as *S. dysgalactiae* (including the subspecies *Dysgalactiae* and *Equisimilis*) by the present immunogenic compositions generally results in a diminishing of bacterial growth and/or one or more of the clinical symptoms associated with streptococcal infection, including arthritis, endocarditis, meningitis, polyserositis, bronchopneumonia, meningitis, permanent hearing loss and septic shock.

The methods disclosed herein may include inducing an immune response against one or more pathogens that include a species of *Streptococcus* (e.g., *Streptococcus dysgalactiae, S. dysgalactiae* sub. *Equisimilis, S. dysgalactiae* sub. *Dysgalactiae, S. pyogenes, S. agalactiae, S. anginosus, S. constellatus, S. equisimilis* and *S. intermedius*.) For example, the methods may include inducing polyclonal antibody production against one or more streptococcal pathogens such as e.g. *S. dysgalactiae* sub. *Equisimilis*. In some embodiments, the methods include administering to a subject a composition that includes an isolated Group C or Group G streptococcal ORF 554 polynucleotide or PPI polypeptide.

Various tests are used to assess the in vitro immunogenicity of the polypeptides of the invention. For example, an in vitro opsonic assay is conducted by incubating together a mixture of *Streptococcus sp.* cells, heat inactivated serum containing specific antibodies to the polypeptide in question, and an exogenous complement source. Opsonophagocytosis proceeds during incubation of freshly isolated polymorphonuclear cells (PMN's) and the antibody/complement/*Streptococcus sp.* cell mixture. Bacterial cells that are coated with antibody and complement are killed upon opsonophagocytosis. Colony forming units (cfu) of surviving bacteria that escape from opsonophagocytosis are determined by plating the assay mixture. Titers are reported as the reciprocal of the highest dilution that gives ≧50% bacterial killing, as determined by comparison to assay controls. Specimens that demonstrate less than 50% killing at the lowest serum dilution tested (1:8), are reported as having an opsonophagocytosis antibody (OPA) titer of 4. The method described above is a modification of Gray's method (Gray, Conjugate Vaccines Supplement, p. 694-697, 1990).

A test serum control, which contains test serum plus bacterial cells and heat inactivated complement, is included for each individual serum. This control is used to assess whether the presence of antibiotics or other serum components are capable of killing the bacterial strain directly (i.e. in the absence of complement or PMN's). A human serum with known opsonic titer is used as a positive human serum control. The opsonic antibody titer for each unknown serum is calculated as the reciprocal of the initial dilution of serum giving 50% cfu reduction compared to the control without serum.

A whole cell ELISA assay can also be used to assess in vitro immunogenicity and surface exposure of the polypeptide antigen, wherein the bacterial strain of interest is coated onto a plate, such as a 96 well plate, and test sera from an immunized animal is reacted with the bacterial cells. If any antibody specific for the test polypeptide antigen is reactive with a surface exposed epitope of the polypeptide antigen, it can be detected by standard methods known to one skilled in the art.

Any polypeptide demonstrating the desired in vitro activity may then be tested in an in vivo animal challenge model. In some embodiments, immunogenic compositions are used in the immunization of an animal (e.g., a mouse) by methods and routes of immunization known to those of skill in the art (e.g., intranasal, parenteral, intramuscular, oral, rectal, vaginal, transdermal, intraperitoneal, intravenous, subcutaneous, etc.). Following immunization of the animal with a particular *Streptococcus dysgalactiae* immunogenic composition, the animal is challenged with *Streptococcus dysgalactiae* or other streptococcal species and assayed for resistance to *Streptococcus dysgalactiae* or other *Streptococcus spp.* infection.

The Group C or Group G streptococcal PPI/ORF 554 polypeptides and polynucleotides are incorporated into immunogenic compositions suitable for administration to a subject. Such compositions typically comprise the nucleic acid molecule or protein, together with a pharmaceutically acceptable carrier. As used herein the phrase "pharmaceutically acceptable carrier" is intended to include any and all solvents, dispersion media, coatings, antibacterial and antifungal agents, isotonic and absorption delaying agents, excipients and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

An immunogenic composition of the invention is formulated to be compatible with its intended route of administration. Examples of routes of administration include parenteral (e.g., intramuscular, intravenous, intradermal, subcutaneous, intraperitoneal), transmucosal (e.g., oral, rectal, intranasal, vaginal, respiratory) and transdermal (topical). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyetheylene glycol and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and the like. In many cases, isotonic agents are included in the composition, for example, sugars, polyalcohols such as manitol, sorbitol and/ or sodium chloride. Prolonged absorption of the injectable compositions can be brought about by including in the composition an agent which delays absorption, for example, aluminum monostearate and gelatin.

Sterile injectable solutions can be prepared by incorporating the active compound (e.g., a Group C or Group G streptococcal PPI polypeptide, ORF 554 polynucleotide or antibody thereto) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems.

Biodegradable, biocompatible polymers, such as ethylene vinyl acetate, polyanhydrides, polyglycolic acid, collagen, polyorthoesters and polylactic acid can be used as carriers. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Combination immunogenic compositions are provided by combining one or more of the polypeptides of the invention with one or more known streptococcal polysaccharides or polysaccharide-protein conjugates.

The protein component of the polysaccharide-protein conjugates is referred to as a "carrier protein". The term "carrier proteins", as a group include those proteins that are non-toxic, non-reactogenic and obtainable in sufficient amount and purity. Carrier proteins are amenable to standard conjugation procedures. For example, $CRM_{197}$ can be used as the carrier protein. $CRM_{197}$, (Wyeth, Sanford, N.C.) is a non-toxic variant (toxoid) of diphtheria toxin isolated from cultures of *Corynebacterium diphtheria* strain C7 (β197) grown in casamino acids and yeast extract-based medium. $CRM_{197}$ is purified through ultra-filtration, ammonium sulfate precipitation, and ion-exchange chromatography. Other diphtheria toxoids are also suitable for use as carrier proteins.

Other suitable carrier proteins include inactivated bacterial toxins such as tetanus toxoid, pertussis toxoid, cholera toxoid (as described e.g. in WO/2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumolysin, pneumococcal surface protein A (PspA), pneumococcal adhesin protein (PsaA), or *Haemophilus influenzae* protein D, can also be used. Other proteins, such as ovalbumin, keyhole limpet hemocyanin (KLH), bovine serum albumin (BSA) or purified protein derivative of tuberculin (PPD) can also be used as carrier proteins.

Immunogenic compositions comprising polynucleotides are delivered to the recipient by a variety of vectors and expression systems. Such systems include, among others, chromosomal, episomal and virus-derived systems, e.g., vectors derived from bacterial plasmids, attenuated bacteria such as *Salmonella* (U.S. Pat. No. 4,837,151), bacteriophage, transposons, yeast episomes, insertion elements, yeast chromosomal elements, viruses such as vaccinia and other poxviruses, adenovirus, baculoviruses, papova viruses, such as SV40, fowl pox viruses, pseudorabies viruses and retroviruses, alphaviruses such as Venezuelan equine encephalitis virus (U.S. Pat. No. 5,643,576), sindbis virus and semiliki forest virus, nonsegmented negative-stranded RNA viruses such as vesicular stomatitis virus (U.S. Pat. No. 6,168,943), and vectors derived from combinations thereof, such as those derived from plasmid and bacteriophage genetic elements, such as cosmids and phagemids. The expression systems should include control regions that regulate as well as engender expression, such as promoters and other regulatory elements (such as a polyadenylation signal). Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., "Molecular Cloning: A Laboratory Manual" 2nd, ed, Cold Spring Harbor Laboratory, Cold Spring Harbor Laboratory Press, Cold Spring Harbor, N.Y., 1989.

An immunogenic composition of the present invention is typically administered parenterally in unit dosage formulations containing standard, well-known nontoxic physiologically acceptable carriers, adjuvants, and vehicles as desired.

A pharmaceutically acceptable vehicle is understood to designate a compound or a combination of compounds entering into a pharmaceutical or immunogenic composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Carriers include neutral saline solutions buffered with phosphate, lactate, Tris, and the like. When administering viral vectors, one purifies the vector sufficiently to render it essentially free of undesirable contaminants, such as defective interfering adenovirus particles or endotoxins and other pyrogens such that it does not cause any untoward reactions in the individual receiving the vector construct. In some embodiments, the means of purifying the vector involves the use of buoyant density gradients, such as cesium chloride gradient centrifugation.

A carrier can also be a liposome. Means for using liposomes as delivery vehicles are well known in the art (see, e.g. the review by Schwendener R A, Adv. Exp. Med. Biol. 620: 117-128, 2007).

The immunogenic compositions of this invention also comprise a polynucleotide sequence of this invention operably linked to a regulatory sequence that controls gene expression. The polynucleotide sequence of interest is engineered into an expression vector, such as a plasmid, under the control of regulatory elements which will promote expression of the DNA, that is, promoter and/or enhancer elements. In some embodiments, the human cytomegalovirus immediate-early promoter/enhancer is used (U.S. Pat. No. 5,168,062). The promoter may be cell-specific and permit substantial transcription of the polynucleotide only in predetermined cells.

The polynucleotides of the invention are introduced directly into the host either as "naked" DNA (U.S. Pat. No. 5,580,859) or formulated in compositions with facilitating agents, such as bupivacaine and other local anesthetics (U.S. Pat. No. 5,593,972) and cationic polyamines (U.S. Pat. No. 6,127,170.)

In this polynucleotide immunization procedure, the polypeptides of the invention are expressed on a transient basis in vivo; no genetic material is inserted or integrated into the chromosomes of the host. This procedure is to be distinguished from gene therapy, where the goal is to insert or integrate the genetic material of interest into the chromosome. An assay is used to confirm that the polynucleotides administered by immunization do not give rise to a transformed phenotype in the host (e.g., U.S. Pat. No. 6,168,918).

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-α, 1-β, 2, 4, 5, 6, 7, 8, 10,12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, Gly-CAM-1 and MadCAM-1; a member of the integrin family such as LFA-1, $V_LA$-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE); oil-in-water emulsions, such as MF59 (U.S. Pat. No. 6,299,884) (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, Mass.)), and SAF (containing 10% Squalene, 0.4% Tween 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed Bordetella; saponins, such as Stimulon™ QS-21 (Antigenics, Framingham, Mass.), described in U.S. Pat. No. 5,057,540, ISCOMATRIX (CSL Limited, Parkville, Australia), described in U.S. Pat. No. 5,254,339, and immunostimulating complexes (ISCOMS); Mycobacterium tuberculosis; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

Therapeutic Antibodies and Antigen-Binding Polypeptides

The present invention is directed inter alia to treatment of streptococcal infection by administration of therapeutic immunological reagents such as humanized monoclonal antibodies recognizing specific epitopes within a streptococcal PPI to a subject under conditions that generate a beneficial therapeutic response in the subject. "Immunological reagents" include e.g. antibodies, humanized antibodies, antibody fragments, peptides comprising antigen binding elements or CDRs, and the like. "Beneficial therapeutic responses" include e.g. induction of phagocytosis or opsonization of beta hemolytic streptococci. The invention is also directed to use of the disclosed immunological reagents in the manufacture of a medicament for the treatment or prevention of a beta hemolytic streptococcal infection.

In one aspect, the invention provides methods of preventing or treating disease associated with beta hemolytic streptococcal infection in a patient. Some methods of the invention entail administering to a patient an effective dosage of an antibody that specifically binds to a streptococcal PPI epitope. Such methods are particularly useful for preventing or treating beta hemolytic streptococcal disease in subjects. "Subjects" include any vertebrate animal, such as companion animals, farm animals, mammals and humans patients. Exemplary methods include administering an effective dosage of an antibody or antigen binding peptide that binds to a streptococcal PPI. Some embodiments include administering an effective dosage of an antibody or other peptide comprising an antigen recognition site or CDR that specifically binds to an epitope within a streptococcal PPI, such as e.g. a PPI comprising an amino acid sequence of any one or more of SEQ ID NOs: 2, 4, 6, 8, 10 and 11.

In yet another aspect, the invention features administering antibodies or other antigen binding peptides that bind to a streptococcal PPI in the subject and induce a clearing response against a beta hemolytic *streptococcus*. For example, such a clearing response can be effected by Fc receptor mediated phagocytosis.

Therapeutic immunological reagents of the invention are typically substantially pure from undesired contaminants. This means that an immunological reagent is typically at least about 50% w/w (weight/weight) purity, as well as being substantially free from interfering proteins and contaminants. In some embodiments, the immunological reagents are at least about 80% w/w purity. In other embodiments, the immunological reagents are at least 90 or about 95% w/w purity. However, using conventional protein purification techniques, homogeneous peptides of at least 99% w/w purity can be obtained.

The methods can be used on both asymptomatic subjects and those currently showing symptoms of disease. The antibodies used in such methods can be human, humanized, chimeric or nonhuman antibodies, or fragments thereof (e.g., antigen binding fragments, peptides comprising epitope binding regions or CDRs) and can be monoclonal or polyclonal, as described herein.

In another aspect, the invention features administering an antibody with a pharmaceutical carrier as a pharmaceutical composition. Alternatively, the antibody can be administered to a subject by administering a polynucleotide encoding at least one antibody chain. The polynucleotide is expressed to produce the antibody chain in the patient. Optionally, the polynucleotide encodes heavy and light chains of the antibody. The polynucleotide is expressed to produce the heavy and light chains in the patient. In exemplary embodiments, the patient is monitored for level of administered antibody in the blood of the patient.

Subjects amenable to treatment include individuals at risk of disease but not showing symptoms, as well as patients presently showing symptoms. Therefore, the present immunogenic compositions and therapeutic antibodies can be administered prophylactically to the general population. In asymptomatic subjects, treatment can begin at any age. Treatment can be monitored by assaying antibody levels over time. If the immune response or antibody level falls, a booster dosage is indicated.

In prophylactic applications, immunogenic compositions or medicaments are administered to a subject susceptible to, or otherwise at risk of, beta hemolytic streptococcal infection in an amount sufficient to eliminate or reduce the risk, lessen the severity, or delay the outset of the disease, including biochemical, histologic and/or behavioral symptoms of disease associated with the infection, its complications and intermediate pathological phenotypes presenting during development of the disease. In therapeutic applications, compositions or medicaments are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

An amount adequate to accomplish therapeutic or prophylactic treatment is defined as a therapeutically- or prophylactically-effective dose. In both prophylactic and therapeutic regimes, immunological reagents are usually administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Such a response can be an active response, i.e., induced by administration of immunogen (supra), or a passive response, i.e., induced by administration of immunoglobulin or antibody or primed T-cells. Typically, the immune response is monitored and repeated dosages are given if the immune response starts to wane.

Effective doses of the compositions of the present invention, for the treatment of beta hemolytic streptococcal infection vary depending upon many different factors, including means of administration, target site, physiological state of the patient, whether the patient is human or another animal, other medications administered, and whether treatment is prophylactic or therapeutic. Usually, the subject is a human but non-human mammals including transgenic mammals can also be treated. Treatment dosages may need to be titrated to optimize safety and efficacy.

For passive immunization with an antibody, the dosage ranges from about 0.0001 to 100 mg/kg, and more usually 0.01 to 5 mg/kg (e.g., 0.02 mg/kg, 0.1 mg/kg, 0.15 mg/kg, 0.2 mg/kg, 0.25 mg/kg, 0.5 mg/kg, 0.75 mg/kg, 1 mg/kg, 2 mg/kg, etc.), of the host body weight. For example dosages can be about 1 mg/kg body weight or about 10 mg/kg body weight or within the range of 1 to 10 mg/kg. Doses intermediate in the above ranges are also intended to be within the scope of the invention. Subjects can be administered such doses daily, on alternative days, weekly, monthly, every two months, every three months, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1 to 10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. Intervals can also be irregular as indicated by measuring blood levels of antibody to streptococcal PPI in the patient. In some methods, dosage is adjusted to achieve a plasma antibody concentration of 1 to 1000 μg/ml and in some methods 25 to 300 μg/ml. Alternatively, antibody can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding antibodies range from about 10 ng to 1 g, 100 ng to 100 mg, 1 μg to 10 mg, or 30 to 300 μg DNA per patient. Doses for infectious viral vectors vary from 10 to 100, or more, virions per dose.

Therapeutic immunological reagents can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is intravenous infusion or subcutaneous administration, although other routes can be equally effective. The next most common route is intramuscular injection. This type of injection is most typically performed in the arm or leg muscles. In some methods, immunological reagents are injected directly into a particular tissue where deposits have accumulated, for example intracranial injection. Intramuscular injection or intravenous infusion are preferred for administration of antibody. In some methods, antibodies are administered as a sustained release composition or device, such as a microinfusor device (e.g. Medipad™ device; see Meehan et al., Journal of Controlled Release, 46:107-119, 1997.)

As alluded to above, immune responses against beta hemolytic streptococcal infection can be formed in vivo (or ex vivo) by administration of nucleic acids encoding antibodies and their component chains used for passive immunization. Such nucleic acids can be DNA or RNA. A nucleic acid segment encoding an immunological reagent is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, Cur. Opin. Genet. Develop. 3:102 109 (1993)); adenoviral vectors (see, e.g., Bett et al., J. Virol. 67:5911 (1993)); adeno-associated virus vectors (see, e.g., Zhou et al., J. Exp. Med. 179:1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70:508 (1996)), Venezuelan equine encephalitis virus (see Johnston et al., U.S. Pat. No. 5,643,576) and rhabdoviruses, such as vesicular stomatitis virus (see Rose, U.S. Pat. No. 6,168,943) and papillomaviruses (Ohe et al., Human Gene Therapy 6:325 (1995); Woo et al., WO 94/12629 and Xiao & Brandsma, Nucleic Acids. Res. 24, 2630 2622 (1996)).

DNA encoding an antibody or antibody fragment comprising a CDR, or a vector containing the same, can be packaged into liposomes. Suitable lipids and related analogs are described by Eppstein et al., U.S. Pat. No. 5,208,036, Felgner et al., U.S. Pat. No. 5,264,618, Rose, U.S. Pat. No. 5,279,833, and Epand et al., U.S. Pat. No. 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., J. Micro Encap. 14(2):197-210 (1997).

Polynucleotide vectors or naked polynucleotides (e.g., DNA) can be delivered in vivo by administration to an individual patient, typically by systemic administration (e.g., intravenous, intraperitoneal, nasal, gastric, intradermal, intramuscular, subdermal, or intracranial infusion) or topical application (see e.g., Anderson et al., U.S. Pat. No. 5,399, 346). The term "naked polynucleotide" refers to a polynucleotide which is not administered together with a transfection facilitating agent. Naked polynucleotides are sometimes cloned in a plasmid vector. Plasmid vectors can further include transfection facilitating agents such as bupivacaine (Weiner et al., U.S. Pat. No. 5,593,972). DNA can also be administered using a gene gun. See Xiao & Brandsma, supra. The DNA encoding an antibody (or fragment comprising a CDR) is precipitated onto the surface of microscopic metal beads. The microprojectiles are accelerated with a shock wave or expanding helium gas, and penetrate tissues to a depth of several cell layers. For example, The ACCEL™ Gene Delivery Device, i.e., a DNA gun, manufactured by Agricetus, Inc. Middleton Wis. is suitable for use in the practice of this invention. Alternatively, naked DNA can pass through skin into the blood stream simply by spotting the DNA onto skin with chemical or mechanical irritation (see Howell et al., WO 95/05853).

In another embodiment, vectors encoding immunological reagents can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Immunological reagents of the invention can optionally be administered in combination with other agents that are at least partly effective in treatment of beta-hemolyic streptococcal disease. Immunological reagents of the invention can also be administered in combination with other agents that enhance access of the therapeutic immunological reagent to a target cell or tissue, for example, liposomes and the like. Coadministering such agents can decrease the dosage of a therapeutic immunological reagent (e.g., therapeutic antibody or antibody chain) needed to achieve a desired effect.

Immunological reagents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as Latex Functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, immunological reagents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527

(1990) and Hanes, Advanced Drug Delivery Reviews 28:97 (1997)). The immunological reagents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1% to 2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10% to 95% of active ingredient, preferably 25% to 70%.

Alternatively, transdermal delivery can be achieved using a skin patch or using transferosomes (Paul et al., Eur. J. Immunol. 25:3521 (1995); Cevc et al., Biochem. Biophys. Acta 1368:201 15 (1998)).

The invention also provides methods of monitoring treatment in a patient suffering from or susceptible to beta hemolytic streptococcal infection, i.e., for monitoring a course of treatment being administered to a patient. The methods can be used to monitor both therapeutic treatment on symptomatic patients and prophylactic treatment on asymptomatic patients. In particular, the methods are useful for monitoring passive immunization (e.g., measuring level of administered antibody).

Some methods entail determining a baseline value, for example, of an antibody level or profile in a patient, before administering a dosage of immunological reagent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the immunological reagent has achieved a desired response). If the value for immune response does not change significantly, or decreases, a negative treatment outcome is indicated. If the treatment is passive immunotherapy, the antibody level is expected to decrease over time with a characteristic half-life.

The tissue sample for analysis is typically blood, plasma, serum, mucous fluid or cerebrospinal fluid from the patient. The sample is analyzed, for example, for levels or titers of antibodies to streptococcal PPI. ELISA methods of detecting antibodies specific to streptococcal PPI are described in the Examples section. In some methods, the level or titer of an administered antibody is determined using a clearing assay, for example, in an in vitro phagocytosis assay (see, e.g., Jansen et al., Clin. Diagn. Lab. Immunol., 8(2): 245-250, 2001.)

The antibody profile following passive immunization typically shows an immediate peak in antibody concentration followed by an exponential decay. Without a further dosage, the decay approaches pretreatment levels within a period of days to months depending on the half-life of the antibody administered.

In some methods, a baseline measurement of antibody to streptococcal PPI in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

Additional methods include monitoring, over the course of treatment, any art-recognized physiologic symptom routinely relied on by researchers or physicians to diagnose or monitor streptococcal infections or associated diseases. For example, one can monitor symptoms of cellulitis, erysipelas, impetigo, necrotizing fasciitis, sore throat, red throat, chills, fever, headache, nausea, vomiting, rapid heartbeat, malaise, swollen tonsils. enlarged lymph nodes and/or rash.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

Example 1

Cloning of S. Dysgalactiae ORF 554

Twelve (12) genome sequences for Group A and multiple genome sequences for Group B streptococcal species are publicly available. The DNA and protein sequences of open reading frame (ORF) number 554 (ORF 554) have been identified in many of these streptococcal genomes; see, for example, published International patent application number WO 02/083859. However, limited sequence information exists on the Group C and G genomes. Disclosed herein are the sequences of this ORF 554 in other group G and C streptococci strains.

Known streptococcal sequences containing ORF554 were aligned in AlignX (Vector NTI) and regions of homology were used for degenerate primer construction (see Wessner, Science, 286 (5554):1495-1496, 1999; Henikoff and Henikoff, Proc. Natl. Acad. Sci. USA, 89:10915-10919, 1992; and Rhee et al., Applied and Environmental Microbiology, 71(2): 817-825, 2005.) Oligonucleotide primers were designed to have minimal degeneracy while maintaining a high melting temperature and low self dimerization potential. The oligonucleotide primer nucleotide sequences used to isolate, amplify and identify the novel Group C or Group G Streptococcal ORF 554 polynucleotides are set forth in SEQ ID NOs: 18-26.

Initial PCR studies were performed using genomic DNA preparations made to a Streptococcus C isolate ATCC12394 (Streptococcus dysgalactiae subspecies Equisimilis). Partial gene sequences were obtained to the 5-prime and 3-prime ends of ORF554. Forward and reverse primers (SEQ ID NO: 23 and SEQ ID NO: 24, respectively) were then designed based on these sequences and were subsequently used to generated by PCR approximately 700-900 bp of sequence of ORF554 from different G and C strains.

No genomic or protein sequences of ORF554 from these strains have been defined prior to this disclosure. The nucleotide sequence obtained for ORF 554 from isolate ATCC12394 is depicted in SEQ ID NO:1, and its amino acid sequence is depicted in SEQ ID NO:2.

ORF554 was found in five (5) isolates: ATCC12394, ATCC35666 and ATCC27823, which were obtained from ATCC, and two Lancefield group G isolates N04A27 and N04AFT, which were obtained as part of a preclinical screen [study No. 6122K1-9000, Cross Sectional Serology Study, Australia, F. Laudat, MD, Paris]. Their respective nucleotide sequences are depicted in SEQ ID NOs: 1, 3, 5, 7, 9, 25, 27, 29 and 31. Their respective amino acid sequences are depicted in SEQ ID NOs: 2, 4, 6, 8, 10, 26, 28, 30 and 32. A consensus amino acid sequence was created between the SEQ ID NOs: 2, 4, 6, 8 and 10 and is presented as SEQ ID NO:11.

Alignment and Clustal W analysis (Chenna et al., *Nuc. Acids Res.*, 31, 3497-3500 (2003)) of the protein and nucleic acid sequences between the novel Group C or Group G Streptococcal PPI and ORF 554 sequences and the known group A and group B streptococcal PPI and ORF 554 sequences provided the percentages which are summarized in Table 1.

TABLE 1

PERCENT IDENTITIES

| A: Amino acid identities | | | B: Nucleotide identities | | |
|---|---|---|---|---|---|
| | GAS | GBS | SEQ ID NO: 10 | GAS | GBS | SEQ ID NO: 9 |
| GAS | 100 | 56 | 76 | GAS | 100 | 52 | 76 |
| GBS | | 100 | 57 | GBS | | 100 | 53 |
| SEQ ID NO: 10 | | | 100 | SEQ ID NO: 9 | | | 100 |

Example 2

Antibodies to Group C/G Staphylococcal PPI Epitopes

The binding of antibodies to bacteria, a process known as opsonization, can lead to uptake and killing of the bacteria by phagocytic cells. Such antibodies, whether derived from bulk human or animal sources, or human or murine or chimeric monoclonal sources, and used alone or in combination, could be used in either prophylactic or therapeutic settings where BHS might be present in the bloodstream, such as neonatal sepsis or sepsis following surgery or leaking of an abscess.

Antibodies were raised in mice against recombinant Group C or Group G staphylococcal peptidyl-prolyl isomerase polypeptides encoded by ORF 554. In the course of screening those anti-beta hemolytic-streptococcal antisera and monoclonal antibodies against various beta hemolytic streptococcal (BHS) strains, it was noted that some antisera and antibodies are cross-reactive against many BHS strains, including members of *Streptococcus pyogenes* (Group A streptococci), *Streptococcus agalactiae* (Group B streptococci) and Group C and Group G streptococci (which include the streptococcal species *Streptococcus anginosus, Streptococcus constellatus, Streptococcus intermedius, Streptococcus dysgalactiae* sub. *Equisimilis* and *Streptococcus dysgalactiae* sub. *Dysgalactiae*) (Table 2.) Screening of the antibodies was performed by fluorescence activated cell sorting (FACS). Briefly, heat killed streptococci were incubated with a mouse anti-Group C and Group G streptococcal PPI antibody on ice for 45 minutes, followed by two washes. The streptococci were then incubated with a goat anti-mouse-Alexa-488 antibody (Molecular Probes, Eugene, Oreg.) for 30 minutes on ice, followed by two washes. Cells thus treated were run on a FACS machine (e.g. see DeMaster et al., Infect. Immun., 70(1): 350-359, 2002.) This cross-reactivity also means that Group C or Group G ORF554 or the polypeptide encoded thereby may be used in an immunogenic composition to induce an immune response effective to protect against infection by Group A or Group B *Streptococcus*, as well as by Group C or Group G *Streptococcus*.

Table 2 depicts the cross reactivity of anti-sera and antibodies to the Group C or Group G Streptococcal PPI encoded by ORF 554. According to Table 2, the symbol "+" means that the antibodies react to the antigen at least three-fold over background; the symbol "±" means that the antibodies react to the antigen between two-fold and three-fold over background; and the symbol "–" means that the detection of antibody signal is at or below background.

TABLE 2

ANTIBODY CROSS-REACTIVITY

| Strain | Species | Reactivity to αPPI |
|---|---|---|
| GAR 1165 | *Streptococcus pyogenes* | + |
| GAR 1199 | *Streptococcus pyogenes* | + |
| GAR 1251 | *Streptococcus pyogenes* | + |
| GAR 1278 | *Streptococcus pyogenes* | + |
| GAR 1362 | *Streptococcus pyogenes* | + |
| GAR 1439 | *Streptococcus pyogenes* | + |
| GAR 1530 | *Streptococcus pyogenes* | + |
| GAR 1566 | *Streptococcus pyogenes* | + |
| GAR 1672 | *Streptococcus pyogenes* | + |
| GAR 1839 | *Streptococcus pyogenes* | + |
| GAR 1923 | *Streptococcus pyogenes* | + |
| GAR 2107 | *Streptococcus pyogenes* | + |
| GAR 2330 | *Streptococcus pyogenes* | + |
| GAR 2646 | *Streptococcus pyogenes* | + |
| GAR 2650 | *Streptococcus pyogenes* | + |
| GAR 2869 | *Streptococcus pyogenes* | + |
| GAR 3104 | *Streptococcus pyogenes* | + |
| GAR 3549 | *Streptococcus pyogenes* | + |
| GAR 3784 | *Streptococcus pyogenes* | + |
| GAR 4029 | *Streptococcus pyogenes* | + |
| GAR 4030 | *Streptococcus pyogenes* | + |
| GAR 4230 | *Streptococcus pyogenes* | + |
| GAR 4773 | *Streptococcus pyogenes* | + |
| GAR 4983 | *Streptococcus pyogenes* | + |
| GAR 4987 | *Streptococcus pyogenes* | + |
| GAR 5861 | *Streptococcus pyogenes* | + |
| GAR 5991 | *Streptococcus pyogenes* | + |
| GAR 6084 | *Streptococcus pyogenes* | + |
| GAR 7055 | *Streptococcus pyogenes* | + |
| GS20 | *Streptococcus pyogenes* | + |
| GS21 | *Streptococcus pyogenes* | + |
| GS22 | *Streptococcus pyogenes* | + |
| GS23 | *Streptococcus pyogenes* | + |
| GS24 | *Streptococcus pyogenes* | + |
| GS25 | *Streptococcus pyogenes* | + |
| GS26 | *Streptococcus pyogenes* | + |
| GS27 | *Streptococcus pyogenes* | + |
| GS28 | *Streptococcus pyogenes* | + |
| GS29 | *Streptococcus pyogenes* | + |
| GS30 | *Streptococcus pyogenes* | + |
| GS31 | *Streptococcus pyogenes* | +/– |
| GS32 | *Streptococcus pyogenes* | + |
| GS33 | *Streptococcus pyogenes* | + |
| GS34 | *Streptococcus pyogenes* | + |
| GS35 | *Streptococcus pyogenes* | + |
| GS36 | *Streptococcus pyogenes* | +/– |
| GS37 | *Streptococcus pyogenes* | + |
| GS38 | *Streptococcus pyogenes* | + |
| GS39 | *Streptococcus pyogenes* | + |
| GS40 | *Streptococcus pyogenes* | + |
| GS41 | *Streptococcus pyogenes* | + |

TABLE 2-continued

ANTIBODY CROSS-REACTIVITY

| Strain | Species | Reactivity to αPPI |
|---|---|---|
| GS42 | Streptococcus pyogenes | + |
| GS43 | Streptococcus pyogenes | + |
| GS44 | Streptococcus pyogenes | + |
| GS45 | Streptococcus pyogenes | + |
| GS46 | Streptococcus pyogenes | + |
| GS47 | Streptococcus pyogenes | + |
| GS 48 | Streptococcus pyogenes | + |
| GS 49 | Streptococcus pyogenes | + |
| GS 50 | Streptococcus pyogenes | + |
| GS 51 | Streptococcus pyogenes | + |
| GS 52 | Streptococcus pyogenes | + |
| GS 53 | Streptococcus pyogenes | + |
| GS 54 | Streptococcus pyogenes | +/− |
| GS 55 | Streptococcus pyogenes | + |
| GS 56 | Streptococcus pyogenes | + |
| GS 57 | Streptococcus pyogenes | + |
| GS 58 | Streptococcus pyogenes | + |
| GS 59 | Streptococcus pyogenes | + |
| GS 60 | Streptococcus pyogenes | + |
| GS 61 | Streptococcus pyogenes | + |
| GS 62 | Streptococcus pyogenes | + |
| GS 63 | Streptococcus pyogenes | + |
| GS 64 | Streptococcus pyogenes | + |
| GS 65 | Streptococcus pyogenes | + |
| GS 66 | Streptococcus pyogenes | + |
| GAR 1 | Streptococcus agalactiae | + |
| GAR 1012 | Streptococcus agalactiae | +/− |
| GAR 1023 | Streptococcus agalactiae | − |
| GAR 1049 | Streptococcus agalactiae | − |
| GAR 10895 | Streptococcus agalactiae | − |
| GAR 1192 | Streptococcus agalactiae | +/− |
| GAR 127 | Streptococcus agalactiae | − |
| GAR 12790 | Streptococcus agalactiae | − |
| GAR 1305 | Streptococcus agalactiae | − |
| GAR 131 | Streptococcus agalactiae | − |
| GAR 1355 | Streptococcus agalactiae | − |
| GAR 1446 | Streptococcus agalactiae | − |
| GAR 1494 | Streptococcus agalactiae | − |
| GAR 154 | Streptococcus agalactiae | + |
| GAR 176 | Streptococcus agalactiae | − |
| GAR 18 | Streptococcus agalactiae | + |
| GAR 1844 | Streptococcus agalactiae | − |
| GAR 1931 | Streptococcus agalactiae | − |
| GAR 2369 | Streptococcus agalactiae | − |
| GAR 252 | Streptococcus agalactiae | − |
| GAR 2533 | Streptococcus agalactiae | − |
| GAR 2682 | Streptococcus agalactiae | + |
| GAR 2717 | Streptococcus agalactiae | − |
| GAR 2723 | Streptococcus agalactiae | − |
| GAR 2724 | Streptococcus agalactiae | − |
| GAR 2842 | Streptococcus agalactiae | +/− |
| GAR 287 | Streptococcus agalactiae | − |
| GAR 3003 | Streptococcus agalactiae | − |
| GAR 3751 | Streptococcus agalactiae | − |
| GAR 381 | Streptococcus agalactiae | − |
| GAR 3830 | Streptococcus agalactiae | − |
| GAR 4131 | Streptococcus agalactiae | +/− |
| GAR 4293 | Streptococcus agalactiae | − |
| GAR 4398 | Streptococcus agalactiae | − |
| GAR 462 | Streptococcus agalactiae | − |
| GAR 4837 | Streptococcus agalactiae | +/− |
| GAR 54 | Streptococcus agalactiae | − |
| GAR 562 | Streptococcus agalactiae | + |
| GAR 6016 | Streptococcus agalactiae | + |
| GAR 614 | Streptococcus agalactiae | + |
| GAR 63 | Streptococcus agalactiae | + |
| GAR 6332 | Streptococcus agalactiae | +/− |
| GAR 6387 | Streptococcus agalactiae | + |
| GAR 6505 | Streptococcus agalactiae | + |
| GAR 67 | Streptococcus agalactiae | − |
| GAR 864 | Streptococcus agalactiae | +/− |
| GAR 967 | Streptococcus agalactiae | − |
| GS19 | GGS | +/− |
| GS27 | GGS | +/− |
| ATCC 33397 | Streptococcus anginosus | +/− |
| ATCC 33397 | Streptococcus anginosus | − |
| GAR 10823 | Streptococcus anginosus | +/− |
| GAR 1272 | Streptococcus anginosus | − |
| GAR 1370 | Streptococcus anginosus | − |
| GAR 1425 | Streptococcus anginosus | +/− |
| GAR 1592 | Streptococcus anginosus | − |
| GAR 1595 | Streptococcus anginosus | − |
| GAR 2044 | Streptococcus anginosus | − |
| GAR 2523 | Streptococcus anginosus | − |
| GAR 2565 | Streptococcus anginosus | − |
| GAR 2697 | Streptococcus anginosus | +/− |
| GAR 2822 | Streptococcus anginosus | +/− |
| GAR 3091 | Streptococcus anginosus | − |
| GAR 3560 | Streptococcus anginosus | + |
| GAR 3576 | Streptococcus anginosus | − |
| GAR 3858 | Streptococcus anginosus | +/− |
| GAR 3938 | Streptococcus anginosus | − |
| GAR 4133 | Streptococcus anginosus | − |
| GAR 4158 | Streptococcus anginosus | + |
| GAR 4234 | Streptococcus anginosus | − |
| GAR 4426 | Streptococcus anginosus | +/− |
| GAR 4680 | Streptococcus anginosus | +/− |
| GAR 4834 | Streptococcus anginosus | − |
| GAR 4896 | Streptococcus anginosus | + |
| GAR 5093 | Streptococcus anginosus | − |
| GAR 5094 | Streptococcus anginosus | +/− |
| GAR 5675 | Streptococcus anginosus | − |
| GAR 5776 | Streptococcus anginosus | + |
| GAR 5831 | Streptococcus anginosus | − |
| GAR 6187 | Streptococcus anginosus | +/− |
| GAR 6590 | Streptococcus anginosus | +/− |
| GAR 7000 | Streptococcus anginosus | +/− |
| GAR 7023 | Streptococcus anginosus | +/− |
| GAR 7190 | Streptococcus anginosus | − |
| GAR 7214 | Streptococcus anginosus | + |
| GAR 7468 | Streptococcus anginosus | − |
| GAR 7818 | Streptococcus anginosus | + |
| GAR 8620 | Streptococcus anginosus | + |
| GAR 8693 | Streptococcus anginosus | +/− |
| GAR 8722 | Streptococcus anginosus | − |
| GAR 8736 | Streptococcus anginosus | − |
| GAR 8954 | Streptococcus anginosus | +/− |
| ATCC 27823 | Streptococcus constellatus | +/− |
| GAR 1235 | Streptococcus constellatus | − |
| GAR 1384 | Streptococcus constellatus | + |
| GAR 1811 | Streptococcus constellatus | + |
| GAR 2421 | Streptococcus constellatus | +/− |
| GAR 3145 | Streptococcus constellatus | − |
| GAR 3355 | Streptococcus constellatus | − |
| GAR 4048 | Streptococcus constellatus | +/− |
| GAR 4083 | Streptococcus constellatus | +/− |
| GAR 4861 | Streptococcus constellatus | + |
| GAR 4870 | Streptococcus constellatus | +/− |
| GAR 5757 | Streptococcus constellatus | − |
| GAR 6129 | Streptococcus constellatus | + |
| GAR 6147 | Streptococcus constellatus | − |
| GAR 6258 | Streptococcus constellatus | +/− |
| GAR 7224 | Streptococcus constellatus | + |
| GAR 7369 | Streptococcus constellatus | + |
| ATCC 12394 | Streptococcus dysgalactiae | + |
| ATCC 12394 | Streptococcus dysgalactiae | + |
| ATCC 40378 | Streptococcus dysgalactiae | − |
| ATCC 40378 | Streptococcus dysgalactiae | − |
| GAR 3868 | Streptococcus dysgalactiae | +/− |
| GAR 4272 | Streptococcus dysgalactiae | + |
| ATCC 35666 | Streptococcus dysgalactiae sub. Equisimilis | + |
| BAA-338 | Streptococcus dysgalactiae sub. Equisimilis | − |
| GAR 3015 | Streptococcus equisimilis | + |
| ATCC 27335 | Streptococcus intermedius | + |
| ATCC 27335 | Streptococcus intermedius | + |
| GAR 2407 | Streptococcus intermedius | +/− |
| GS28 | unk | + |
| GS67 | GGS/GCS | + |

TABLE 2-continued

ANTIBODY CROSS-REACTIVITY

| Strain | Species | Reactivity to αPPI |
|---|---|---|
| GS68 | GGS/GCS | +/− |
| GS69 | GGS/GCS | +/− |
| GS70 | GGS/GCS | +/− |
| GS71 | GGS/GCS | + |
| GS72 | GGS/GCS | + |
| GS73 | GGS/GCS | +/− |
| GS74 | GGS/GCS | − |
| GS75 | GGS/GCS | +/− |
| GS77 | GGS/GCS | + |
| GS78 | GGS/GCS | +/− |
| GS79 | GGS/GCS | +/− |
| GS80 | GGS/GCS | − |
| GS81 | GGS/GCS | − |
| GS82 | GGS/GCS | +/− |
| GS83 | GGS/GCS | + |
| GS84 | GGS/GCS | − |
| GS85 | GGS/GCS | +/− |
| GS86 | GGS/GCS | +/− |
| GS88 | GGS/GCS | + |
| GS89 | GGS/GCS | +/− |
| GS90 | GGS/GCS | − |
| GS91 | GGS/GCS | +/− |
| GS92 | GGS/GCS | + |
| GS93 | GGS/GCS | + |
| GS94 | GGS/GCS | + |

What is claimed is:

1. An isolated polypeptide that comprises an amino acid sequence that is at least 90% identical to the amino acid sequence of SEQ ID NO: 11.

2. The isolated polypeptide of claim 1, wherein the polypeptide comprises the amino acid sequence of SEQ ID NO: 11.

3. An immunogenic composition comprising an isolated polypeptide that comprises:

a) an amino acid sequence that is 90% identical to the amino acid sequence of SEQ ID NO: 11; or b) the amino acid sequence of SEQ ID NO: 11.

4. A kit comprising an isolated polypeptide that comprises an amino acid sequence that is 90% identical to the amino acid sequence of SEQ ID NO: 11.

* * * * *